United States Patent [19]
Berta

[11] Patent Number: 5,466,290
[45] Date of Patent: Nov. 14, 1995

[54] DRYING SYSTEMS FOR APPARATUS FOR GELATIN COATING TABLETS

[75] Inventor: Norbert I. Berta, Devon, Pa.

[73] Assignee: McNeil-PPC, Inc., Milltown, N.J.

[21] Appl. No.: 3,347

[22] Filed: Jan. 12, 1993

Related U.S. Application Data

[63] Continuation-in-part of Ser. No. 609,482, Nov. 5, 1990, Pat. No. 5,228,916.
[51] Int. Cl.[6] ............................. A23G 3/24; B05C 3/02; B05C 13/02; F26B 19/00
[52] U.S. Cl. .............................. 118/20; 118/30; 118/426; 118/500; 118/58; 118/66; 427/2.14; 34/194; 34/206; 34/209
[58] Field of Search ................................. 118/16, 18, 20, 118/30, 425, 426, 500, 503, 58, 64, 66, 67; 427/3, 2.14; 34/68, 193, 194, 206, 204, 209

[56] References Cited

U.S. PATENT DOCUMENTS

| 1,123,934 | 1/1915 | Schrafft et al. | 118/20 |
| 1,377,644 | 5/1921 | Warrington | 34/194 |
| 2,795,056 | 6/1957 | Remer | 34/206 |
| 2,889,801 | 6/1959 | Pikal | 118/30 |
| 2,995,482 | 8/1961 | Boyer et al. | 118/58 |
| 4,820,524 | 4/1989 | Berta | 424/474 |
| 4,990,358 | 2/1991 | Berta | 427/3 |
| 5,228,916 | 7/1993 | Berta | 118/30 |
| 5,234,099 | 10/1993 | Berta | 198/803.1 |
| 5,286,007 | 2/1994 | Takagi | 266/96 |
| 5,314,537 | 5/1994 | Berta | 118/30 |

FOREIGN PATENT DOCUMENTS

| 0448231A1 | 9/1991 | European Pat. Off. . |
| 4213936A1 | 11/1992 | Germany . |

Primary Examiner—W. Gary Jones
Assistant Examiner—Steven P. Griffin
Attorney, Agent, or Firm—Bernard F. Plantz

[57] ABSTRACT

The present invention is directed to an apparatus for coating a product such as a medicament in the shape of a tablet. The apparatus includes a plurality of plates for receiving and retaining the products and means for advancing the plates on a conveyor to various processing stations. At a dipping station, a dipping means lowers and raises at least one plate into a first coating tank for coating at least a portion of the product. At a rotating station, a rotation means rotates one of the plates containing the product for spreading the coating on the product. After rotation, a first elevator transfers the plates from the conveyor to a dryer disposed above the conveyor. A second elevator transfers the plates from the dryer back to the conveyor for further processing. The dryer includes complementary acting pusher bars for transporting a plurality of plates horizontally along a plurality of vertically spaced guides. The plates are transported upward to traverse the guides through a first section of the dryer and downward through a second section of the dryer by the combined action of the first and second elevators and a mid-elevator. Several embodiments for the elevator are disclosed which include a lift bar mechanism, a continuous chain mechanism and a lift rod system.

22 Claims, 21 Drawing Sheets

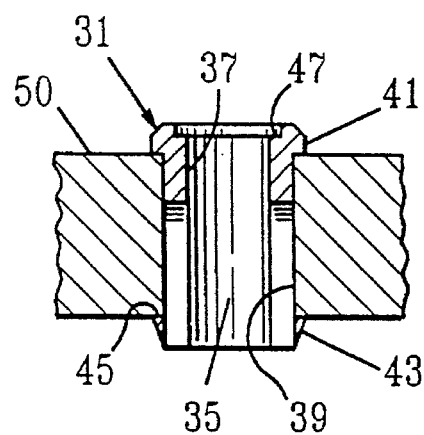
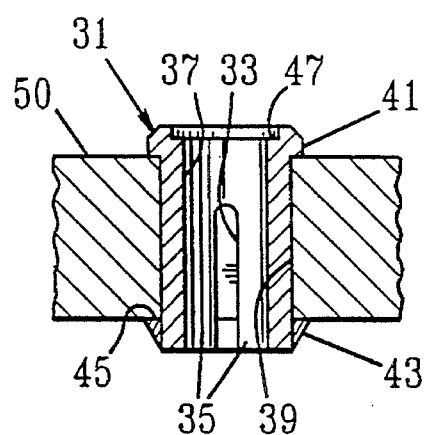
FIG. 7A  FIG. 7B
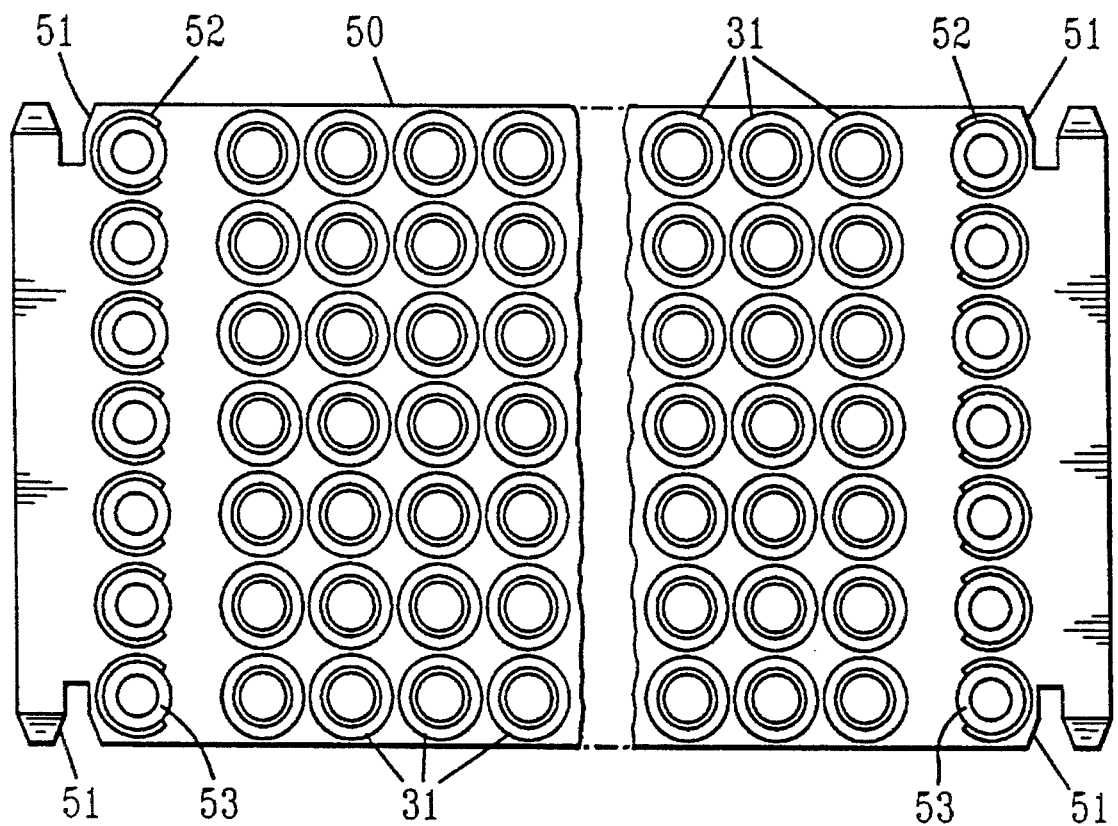
FIG. 8

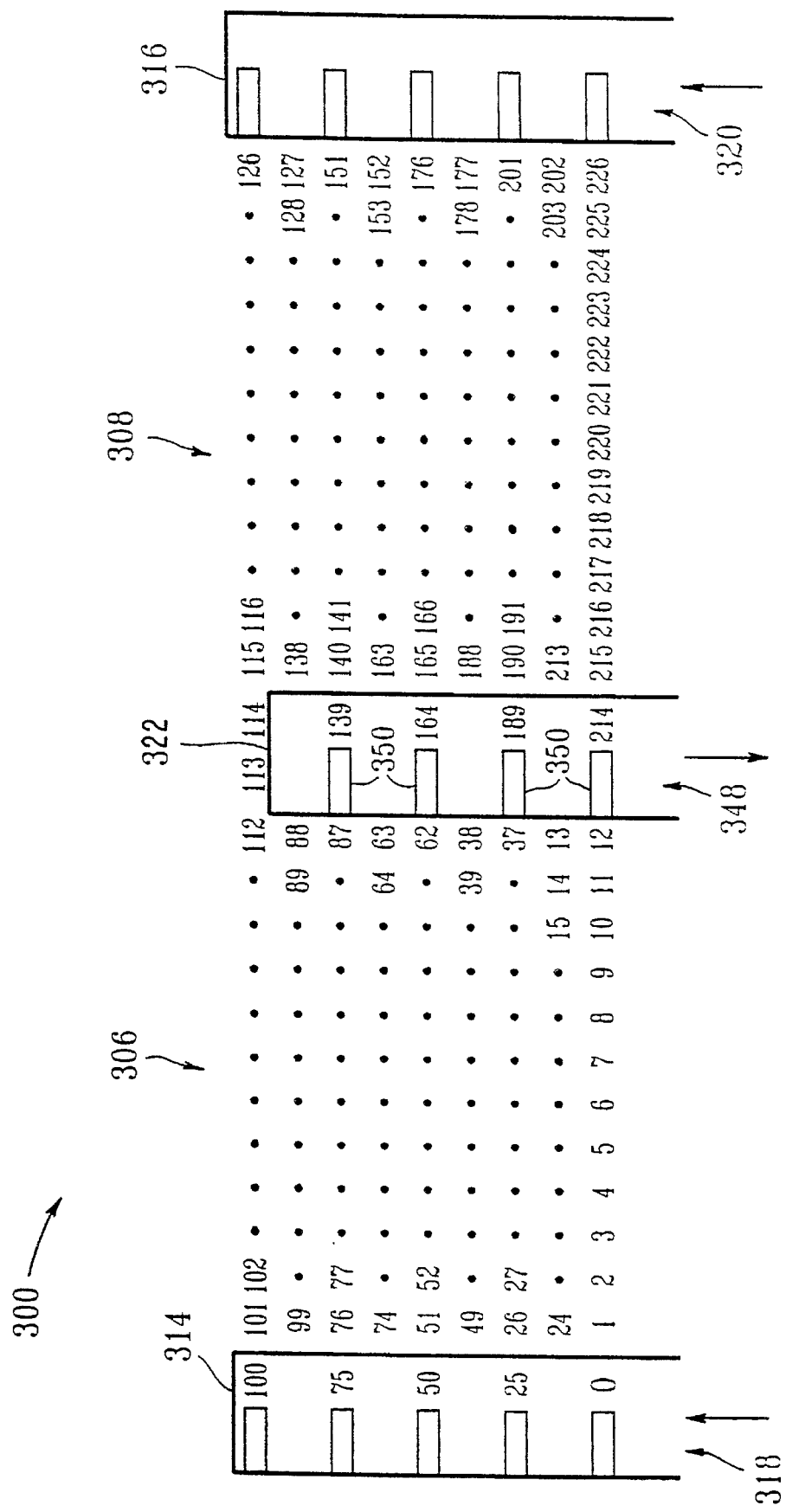

DRYING SYSTEMS FOR APPARATUS FOR GELATIN COATING TABLETS

This application is a continuation-in-part application of my copending application, Ser. No. 609,482, filed Nov. 5, 1990 entitled Methods and Apparatus for Creating a Gelatin coating, now U.S. Pat. No. 5,228,916, which is commonly assigned and which is also hereby incorporated by reference and fully set forth herein.

The present invention is related to my prior patents U.S. Pat. Nos. 4,921,108 issued on May 1, 1990; 4,867,983 issued on Sep. 19, 1989; 4,820,524 issued on Apr. 11, 1989 and 4,966,771 issued on Oct. 30, 1990, and my U.S. patent application Ser. No. 483,159, filed Feb. 22, 1990, now U.S. Pat. No. 5,234,099, which are assigned to the assignee of the present application and incorporated by reference as if fully set forth herein.

The present invention is also related to my U.S. patent applications, Ser. Nos. 08/003,158, 08/003,334, 08/003,348 and 08/003,349 all filed concurrently herewith, which are all assigned to the assignee of the present application and incorporated by reference as if fully set forth herein.

The present invention relates to methods and apparatus for forming a coating on a product and, more particularly, to methods and apparatus for forming a coating comprised of a gelatinous substance on a tablet. The present invention further relates to methods and apparatus for loading tablets into the coating apparatus for processing.

BACKGROUND OF THE INVENTION

Many products, from prescription drugs to commonly available vitamin tablets to candy, are manufactured in a form which may be described as a "tablet." The primary function of a tablet is to provide a single dose or "serving" of the product in a manner which is convenient to manufacture, package and consume. As pointed out in my previous patents and applications, referenced above, it has been found that certain individuals suffer from physiological and psychological problems which impede their ability to swallow tablets. It has also been found that by providing tablets with a smooth coating, such as a coating comprised of gelatin or a gelatinous substance that the "swallowability" of a tablet is greatly enhanced. Such coatings and the general considerations involved in their application, such as preparation and drying time, are well known to those of ordinary skill.

In addition to enhanced swallowability, there are numerous other reasons that it is desirable to provide a coating on a tablet. Such coatings protect the underlying product from deterioration and also serve to permit identifying colors or markings to be incorporated onto the design of the product, promoting product differentiation and brand identification. As pointed out in my previous patents and applications, it is also desirable in some instances to overlap two or more coatings to form a seam, thereby simulating the appearance of a hard gelatin capsule while providing a coated, solid (and thus tamper resistant) product.

Methods and apparatus for applying a gelatinous coating or other coating to a product which is in the form of a tablet are well known to those of ordinary skill. Such methods may include pan dipping or vacuum spraying of the coating material on to the tablet. Such methods are crude, however, producing uneven coatings which are generally unacceptable for commercial use. In an effort to improve the state of the art, the inventions disclosed by my previous patents and applications have provided methods and apparatus whereby individual products are held partially within a sleeve or "collet" and the exposed portion of the product precisely lowered into a dipping tank. As disclosed, bars or plates containing a plurality of product to be dipped are conveyed and rotated and the product itself is manipulated to provide even coatings of high quality and consistency at high volume. These inventions, however, do not permit every type of product such as certain styles of tablets and medicaments to be coated—or at least to be coated in a particular manner. For example, dipping the circular face of a substantially cylindrical tablet whose height is relatively small compared to its diameter would be difficult using the apparatus disclosed by my prior patents and applications, particularly if a circumferential seam is desired. Other examples include the difficulty of coating either a fragile product or applying fragile coating compositions. It has been found that certain coatings will be marred by the friction fit within the collets or similar retaining devices making these unsuitable for use in the apparatus of my prior inventions.

It is known to transport individual tablets or capsules through an immersion coating bath by retaining the tablets on individual vacuum tubes. For example, U.S. Pat. No. 3,896,762—Banker discloses a rotary coating apparatus for pharmaceutical solid dosage forms. Since the surface of the coating is horizontal it is tangential to the path of the tablet; accordingly, Banker discloses that it is necessary to rotate the vacuum tube holding the tablet around its longitudinal axis to achieve an even coating. There are, however, a number of practical shortcomings in the apparatus disclosed. First, although a dryer and ejector are disclosed, the overall system does not lend itself to high volume production or provide for modifications in drying time or inspection, etc. Secondly, the system disclosed by Banker is directed to passing one-half or more of the total depth dimension of the tablet through the coating solution. The tablet is then randomly ejected, with no provision being made to align or otherwise control the orientation of the tablet and the uncoated portion, if any, which exists. Moreover, there is no provision for adjusting the coating to achieve multi-colored or capsule-like coated products. Therefore, one of ordinary skill will appreciate that the system disclosed by Banker is of limited use in current manufacturing environments, where high volume and flexibility are important, along with the need for consistency and high quality.

Therefore, there exists a need for methods and apparatus which can consistently place a precisely defined amount of coating material on an individual product. Such methods and apparatus should be capable of producing coated products at high volume and should possess inherent flexibility to permit new designs and types of coatings to be incorporated without an undue degree of retooling. Moreover, it is extremely important that the products be introduced into the system in a highly controlled manner to enable the coatings to be accurately applied.

SUMMARY OF THE INVENTION

The present invention is directed to an apparatus for coating a product which comprises a plurality of plate means for receiving and retaining the products and means for advancing the plate means on a conveyor to various processing stations. At a dipping station, a dipping means lowers and raises at least one plate into a coating tank for coating at least a portion of the product. At a rotating station, a rotation means rotates one of the plates containing the product for spreading the coating on the product. After rotation, a first elevator means transfers the plates from the conveyor means to a dryer means disposed above the conveyor. The dryer means includes means for transporting a plurality of plates upward through a first section of the dryer and a means for transporting a plurality of plates downward through a second section of the dryer. The plates are transported horizontally along a plurality of vertically spaced guide means and are also transferred vertically between the guide means. A second elevator means transfers the plates from the dryer back to the conveyor for further processing, such as through the same or similar apparatus for applying one or more additional coatings to the product. Several embodiments for the elevator are disclosed which include a lift bar mechanism, a continuous chain mechanism and a lift rod system.

BRIEF DESCRIPTION OF THE DRAWINGS

FIGS. 7a and 7b are cross-sectional views of another embodiment of a tablet holder of the present invention.

FIG. 8 is a plan view of a product carrier plate of one embodiment of the present invention.

FIGS. 12(a)–12(e) are schematic representations of the advancement of coated products through the dryer in accordance with the present invention.

DETAILED DESCRIPTION OF THE PREFERRED EMBODIMENTS

Figure 1:
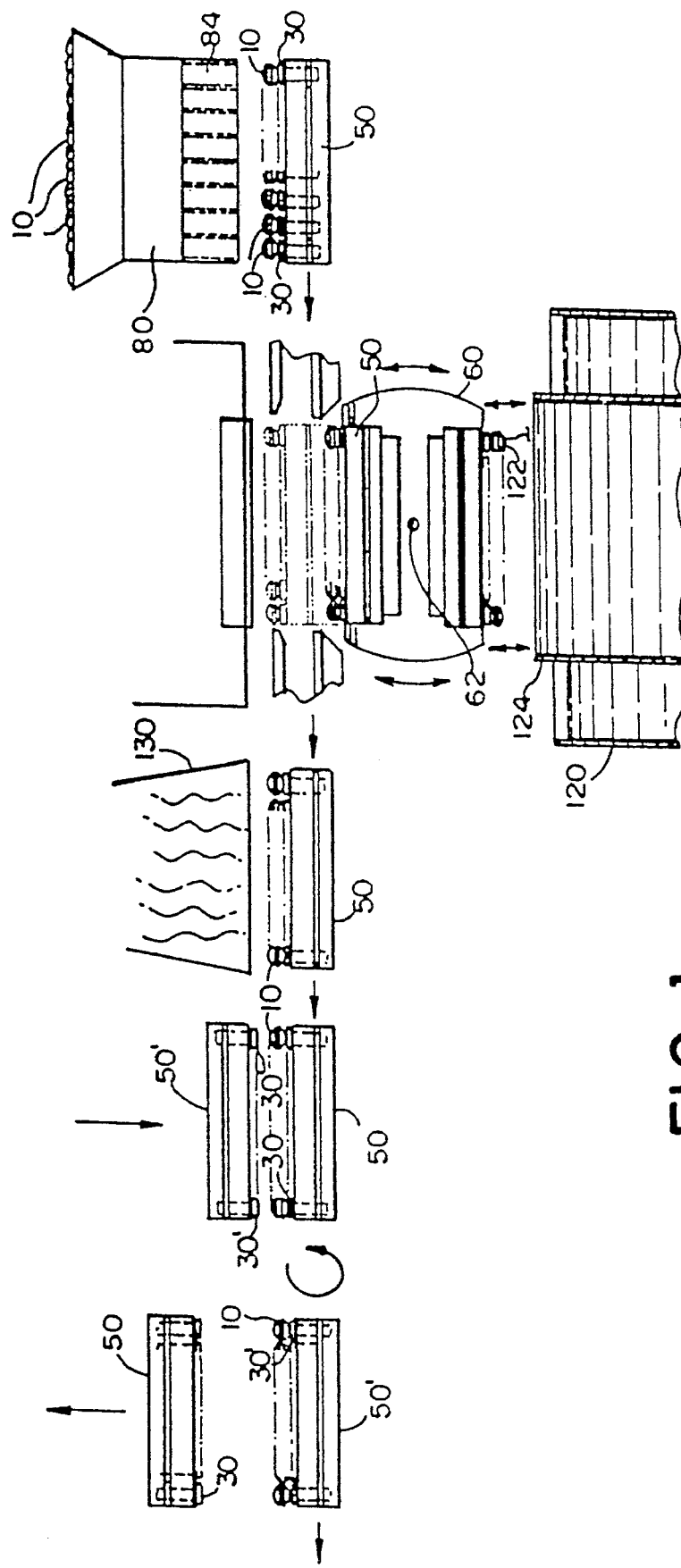
FIG. 1 is a partially diagrammatic, partially schematic representation of the coating apparatus of the present invention.

A generalized representation of the apparatus used in a preferred embodiment of the present invention is shown in FIG. 1. It will be understood that the descriptions set forth may be applied to numerous types and shapes of products. The type of tablet illustrated and the sequence shown are for purposes of explanation only.

A plurality of the product 10 to be coated is placed in a feeder means 80. Preferably, the feeder will be comprised of a hopper and a series of feeder tubes 84 which align, orient. and dispense the product 10 in the appropriate manner. Initially disposed directly beneath the feeder tubes 84 and in registration therewith is a plate 50. The plate 50 has a plurality of tablet holders 30 which, as explained below, restrain the product during certain portions of the coating process. The tablet holders 30 preferably correspond to the feeder tubes 84 and thus, most preferably, each tube 84 feeds a single product 10 into a single tablet holder 30.

Conveyor means 90 transfer the plates 50 from the feeder 80 to the vacuum chamber 60. In a preferred embodiment shown in FIG. 1, the vacuum chamber 60 is adapted to receive and make vacuum tight connections with two plates 50. As shown by the arrows, the vacuum chamber 60 is further provided with manipulating means whereby it may be moved up and down, and rotated about a pivot point 62.

A first dipping tank 120 is disposed beneath the vacuum chamber 60 and is filled with a quantity of coating material. Preferably a coating material such as gelatin is used and, most preferably, the dipping tank 120 is provided with pumps and conduits whereby the coating material is continuously circulated. As illustrated, the dipping tank is most preferably constructed to form a meniscus surface 122 by pumping the coating material into an inner tank 124 which is permitted to overflow into the larger tank 120. Such a system prevents the coating material from hardening while the apparatus is in use and helps to ensure that the coating material presents the same even and substantially level surface to the product being dipped at all times.

In operation, the plate 50 is moved into engagement with the vacuum chamber 60 and then the chamber 60 and the plate 50 are rotated one-half revolution. As explained below, the vacuum chamber 60 creates a vacuum within the tablet holders 30 which holds the product 10 in place and in the correct orientation to be dipped. The vacuum chamber 60 is next lowered into dip tank 120 to a predetermined depth and then withdrawn. The vacuum chamber 60 is then rotated one and one-half revolutions in order to return the plate 50 to its original orientation. The additional full revolution beyond that required provides a dwell time, permitting the coating to initially "set" and also prevents the coating from running or sagging due to gravity by constantly reorienting the product 10. However, a rotation of as little as one-half of a revolution may be adequate in some instances. At this point, the plate 50 may be returned to the conveyor means and removed from the vacuum chamber 60.

The design of the vacuum chamber 60 and placement of the dip tank 120 illustrated permit a wide variety of coatings to be effectively and efficiently achieved. Although the dipping of a substantially cylindrical tablet having concave faces to form a coating having circumferential seam is illustrated, those of ordinary skill will understand that numerous other shapes of product, as well as other coating schemes are possible using the apparatus disclosed. As will be explained below, the shape of the tablet holders 30 and the design of the sub-components of the vacuum chamber 60 may be readily adapted for particular requirements. Also, as illustrated in FIG. 1, throughput may be increased by designing the vacuum chamber 60 to form a vacuum tight seal with further plates 50, such that each time the vacuum chamber 60 is rotated, a plate 50 which has already been lowered into the dipping tank 120 is returned to the conveyor means.

After the plate 50 containing the partially coated product 10 is removed from the vacuum chamber 60 the plate may be passed through a dryer means 130 for curing the coating material. As will be understood by those of ordinary skill, the dryer 130 will be chosen to correspond to the heat and moisture requirements of the coating material being used. Radiant heat, forced hot air, microwave dryers and combinations of these types are among the types available. Depending upon the type of dryer 130 chosen, one or more conveyors and other apparatus may be required to transfer the plates 50 into and out of the dryer 130.

After the coating has been cured, the plate 50 is again returned to conveyor means and is preferably transferred to another location. At this point, although only a portion of each individual product 10 has been coated, it may be desirable to eject the product 10 and consider the process complete. This may be true, for example, where the product has already been coated and the above-described process is carried out to add a second color to a portion of the product.

In a preferred embodiment, however, the present invention provides methods and apparatus which permit the uncoated portion of the product 10 to be coated. First, a second plate 50' is positioned in registration with the product contained on the first plate 50, as illustrated in FIG. 1. The second plate 50' is lowered until the coated side of the product 10 is disposed within the tablet holders 30' of the second plate 5040. The resulting "sandwich" of the first plate 50, the product 10 and the second plate 50' is then rotated one-half revolution by the conveyor/manipulator means. As shown, the positions of the plates 50,50' are thus reversed, and when the first plate 50 is removed the uncoated portion of the product 10 is exposed. The second plate 50' may then be transferred to the starting point of the dipping process and put through the sequence of manipulations necessary to form a coating which were set forth above using either the same apparatus or further apparatus, using either the same coating material or a different coating material.

In the instance where the same apparatus is used to place coating upon the uncoated portion of the product 10, the second plate 50' may be preferably conveyed or otherwise transported to a location just before the vacuum chamber 60, i.e., between the vacuum chamber 60 and the feeder 80 illustrated in FIG. 1. The second plate 50' would simply be inserted into engagement with the vacuum chamber 60 and the above described apparatus would carry out substantially the same sequence of functions in terms of dipping the product 10, curing the coating as needed, etc. After the product 10 has been fully coated and cured, it may be ejected prior to the transfer stage between the first and second plates 50,50'.

In another embodiment of the present invention, after the partially coated product has been transferred to the second plate 50', the plate 50' may enter a duplicate series of apparatus, such as that described above with reference to FIG. 1. In other words, a second vacuum chamber, dipping tank, dryer, and manipulating and conveying apparatus may be provided. After the product 10 is coated and cured using this second set of apparatus, the completed product is ejected.

Figure 2:
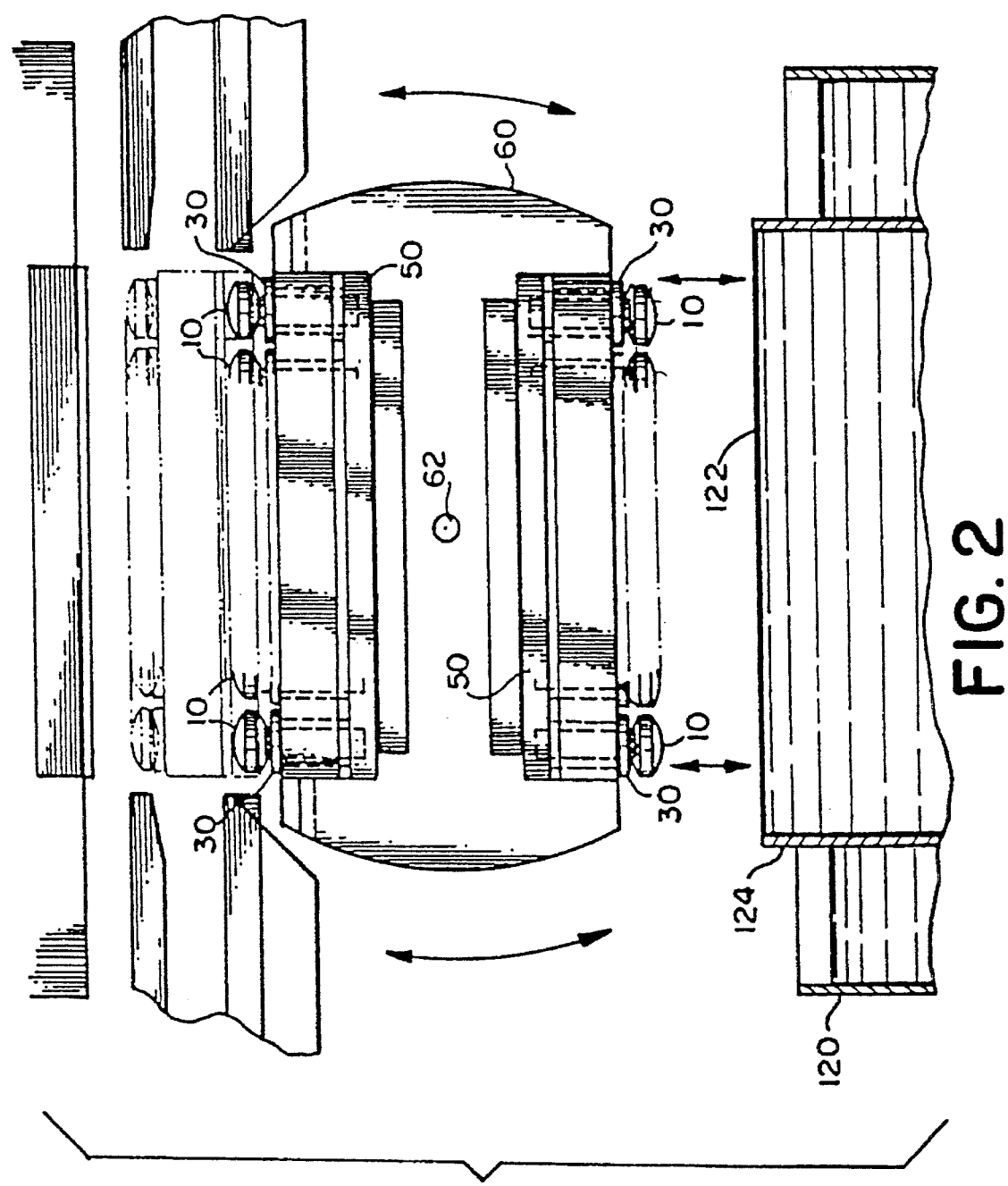
FIG. 2 is a broken away, partially cross-sectioned side view of a portion of the apparatus of FIG. 1.

Referring now to FIG. 2, a more detailed view of the vacuum chamber 60 described above is shown. As explained above, in a preferred embodiment two plates 50 (or 50') are retained in a vacuum tight seal upon the vacuum chamber 60, thereby permitting more efficient indexing between the raising and lowering of the apparatus and the infeed and outfeed of the plates 50 from the vacuum chamber 60.

As shown, the entire chamber may be raised or lowered to bring the product 10 into contact with the surface of the coating material 122. The vertical motion also preferably provides a transfer between the vacuum chamber 60 and the conveyor means, as shown in phantom in FIG. 2. This latter vertical movement also provides clearance when the vacuum chamber 60 is rotated during the dipping process explained above with reference to FIG. 1.

Figure 3:
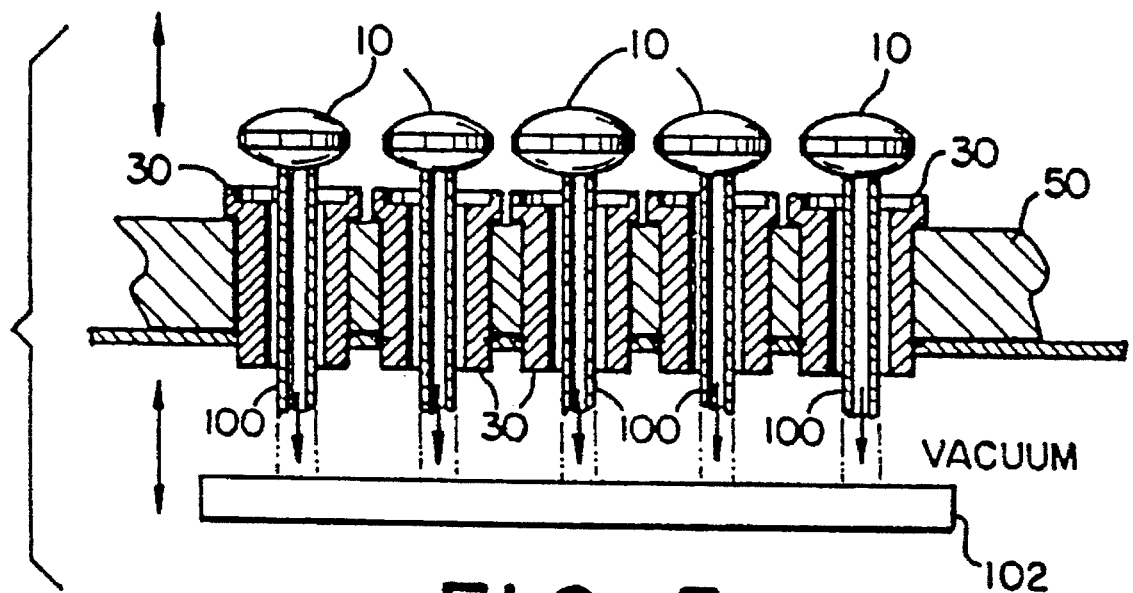
FIG. 3 depicts a cross-sectional view of the tablet holders and plate used in one embodiment of the present invention.

Further details of the vacuum chamber 60 are shown in FIG. 3, which illustrates broken-away section of the plate 50 and the vacuum chamber 60. As seen in cross-section, the plate 50 has a plurality of tablet holders 30 inserted into a series of openings. The plate 50 rests upon the vacuum chamber 60 and forms a seal therewith. A plurality of vacuum tubes 100 extend through the tablet holders 30 and, when in use, engage and slightly lift the product 10 from the tablet holders 30 as shown. The vacuum created within the vacuum chamber 60 is channeled through the vacuum tubes 100 by a manifold or similar means, thereby permitting the vacuum to act upon the surface of the product 10 when contacted by the vacuum tubes 100. By providing vacuum tube actuator means 102 for raising and lowering the vacuum tubes 100 relative to the vacuum chamber 60, the vacuum tubes may be selectively placed in the raised position illustrated. The actuator 102 may be a common bar or mounting structure which is moved by a gear, cam or pulley system.

When in the position illustrated, it is possible to invert or otherwise manipulate the product 10 as described above without friction or the use or mechanically actuated clamps. The vacuum handling system disclosed by the present invention provides a secure retention of the product while minimizing the possibility of damaging either the coating or the product 10 itself. As explained above, the methods and apparatus of the present invention are useful for numerous shapes and sizes of product 10, however, most preferably, the product 10 will have one or more curved surfaces, as illustrated. The curved surfaces permit the tubes 100 to be made from a rigid material such as stainless steel. Those of ordinary skill will realize however, that nearly any shape and any orientation of product may be retained using appropriately designed vacuum tubes. Finally, in certain instances it will be desirable to provide a cushion or resilient tip on the distal end of the vacuum tube in order to ensure a sufficient grip.

Figure 4:
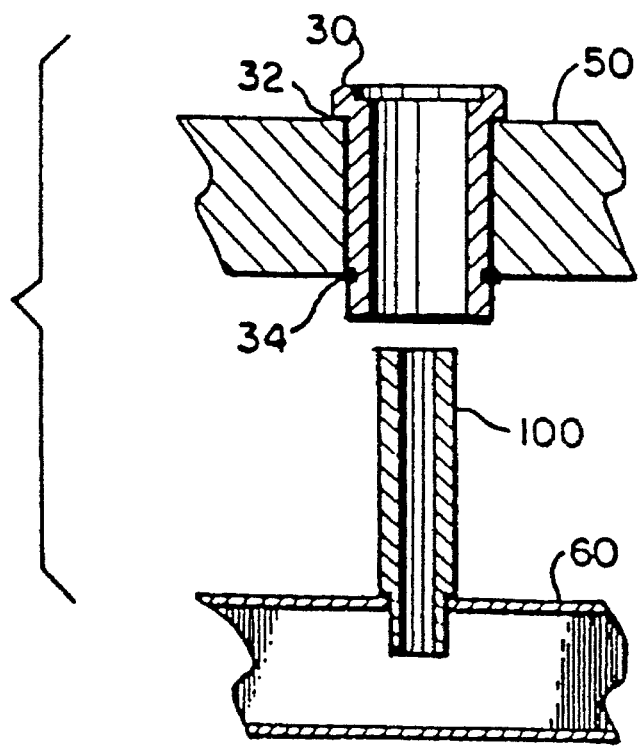
FIG. 4 is a broken away cross-sectional view of the plate of FIG. 3, illustrating the tablet holder and vacuum tube used in one embodiment of the present invention.

Referring now to FIG. 4, one embodiment of the tablet holder 30 is illustrated. A shoulder 32 is formed at a first end of the tablet holder to provide a positive stop. A groove is formed at a second end, into which an "O" ring or the like may be engaged to retain the tablet holder 30 in the plate 50. As will be understood by those of ordinary skill, the tablet holder 30 and the plate 50 may be in certain instances formed as an integral component. FIG. 4 also illustrates the vacuum tube 100 in the withdrawn position. When the vacuum tube 100 is in the withdrawn position, the depression formed in the tablet holder 30 is the only means for restraining the product 10 (not shown in FIG. 4).

FIGS. 7a and 7b show a second embodiment of the tablet holder for use in plates 50. Tablet holder 31 shown in FIGS. 7a and 7b is provided with a plurality of slots 33 forming resilient fingers 35. FIG. 7a is a cross-section taken through the slots 33, and FIG. 7b is a cross-section taken with the holder 31 rotated 90° from its position in FIG. 7a. In the embodiment shown in FIGS. 7a and 7b, a pair of slots 33 are provided thereby forming a pair of resilient fingers 35. Slots 33 are disposed longitudinally through the walls of holder 31. Holder 31 is generally in the form of a cylinder having a central bore 37. Tablet holder 31 is retained in the opening 39 of plate 50 by shoulder portion 41 on one end and angled flange 43 on a second end. For ease in installation the size of upper surface 45 of angled flange 43 may be significantly reduced at the portion of the side walls located immediately adjacent to slots 33 as shown in FIG. 7a. The flange 43 may gradually increase to its largest surface area located 90° from slots 33 as shown in FIG. 7b. The holder 31 is also provided with seat 47 for accepting a tablet therein. It will be understood by those of ordinary skill that the seat 45 may be shaped appropriately to match the shape of the product being held.

The holder 31 is a "push-in" holder that does not require o-rings or the like that are susceptible to wear and tear. In order for the holder 31 to be secured in the plate 50, the outer diameter of the annular resilient fingers 35 forming the cylinder of holder 31 must be slightly larger than the diameter of the opening 39 in plate 50. The angle of flange 43 enables the holder 31 to be inserted through the opening 39 and to cause the fingers 35 to be slightly compressed toward each other as the holder is passed through the plate 50. When the flange 43 clears the opening 39 and plate 50, the resilient fingers 35 spring back to their original position causing flange 43 to engage plate 50 thereby securing the holder 31 therein.

FIG. 8 shows a plan view of a carrier plate 50 for retaining the plurality of product holders 30 or 31. The carrier plate 50 of FIG. 8 includes a plurality of longitudinal rows of individual product holders 31. The plates 50 are preferably from 4 to 5 inches wide and approximately one-half to one inch thick. In one embodiment, the plate 50 is made about 23 to 24 inches in length enabling the plate to include 7 rows each containing 33 holders for a total of 231 holders.

A preferred embodiment of the carrier plate 50 of the present invention is machined from tool plate aluminum. It is also preferred that the aluminum have a protective coating such as an anodized coating applied to the surface. The plate 50 is rectangular and symmetrical, having four easily spaced slots 51 disposed near the four corners which engage the conveyor and/or holding means. Also provided at either end are alignment and transport holes 52 which contain retaining bushings 53 which are used to manipulate the plate 50 as it is advanced through the feeder means 80 and through other processing stations.

The present invention also provides methods for coating a product 10 in accordance with the present invention. A preferred embodiment of the methods of the present invention is illustrated by the sequence of views in FIG. 5. For purposes of illustration and explanation a single product 10, vacuum tube 100 and tablet holder 30 are illustrated, along with broken away portions of other apparatus such as the plate 50. As shown in the upper left section of FIG. 1, a plate 50 containing a tablet holder 30 is positioned beneath the feeder means 80 for feeding a tablet described above and a product 10 is disposed within the tablet holder 30. Next, the plate 50 containing the individual products 10 is moved into the vicinity of the vacuum chamber 60, where it is cleaned of dust and particulate matter. For clarity, the representation of the vacuum chamber 60 is omitted from the other views shown in FIG. 5. An individual vacuum tube 100 is then brought into position and placed in close proximity or contact with the product 10. At this point, the vacuum created within the vacuum tube 100 "picks up" or engages the product 10. After the individual products 10 have been engaged by the vacuum tubes 100, the entire plate 50 is rotated one-half of a revolution, suspending the product 10 by the vacuum tube 100. The vacuum tube 100 and the product 10 attached thereto may now be moved into position and lowered into a coating tank 120. The depth to which the product 10 is lowered is a function of the motion of the vacuum tubes 100 and plate 50, which may be precisely regulated by hydraulic actuators, gear trains or other means for actuating the vacuum tube 100 and/or moving the plate 50. The vacuum tube 100 and the partially coated product 10 are then withdrawn from the coating tank 120, but the product 10 is not fully withdrawn into its holder 30. Instead, the plate 50 and partially extended vacuum tubes 100 are rotated one and one-half revolutions, returning the plate 50 to its initial orientation. The additional revolution provides a dwell, permitting the coating to initially set, as well as aiding in the provided evenness of the coating by preventing the coating from running due to gravity. In certain embodiments, however, this dwell may be unnecessary and the plate need only be rotated one-half of a revolution. After the plate 50 has been returned to its initial position, the vacuum tube 100 may be withdrawn until the product 10 again rests in a holder 30 within the plate 50. Once the vacuum tube 100 has been sufficiently withdrawn, the vacuum connection to the product 10 is broken and gravity and the holder 30 restrain the product 10.

Figure 5:
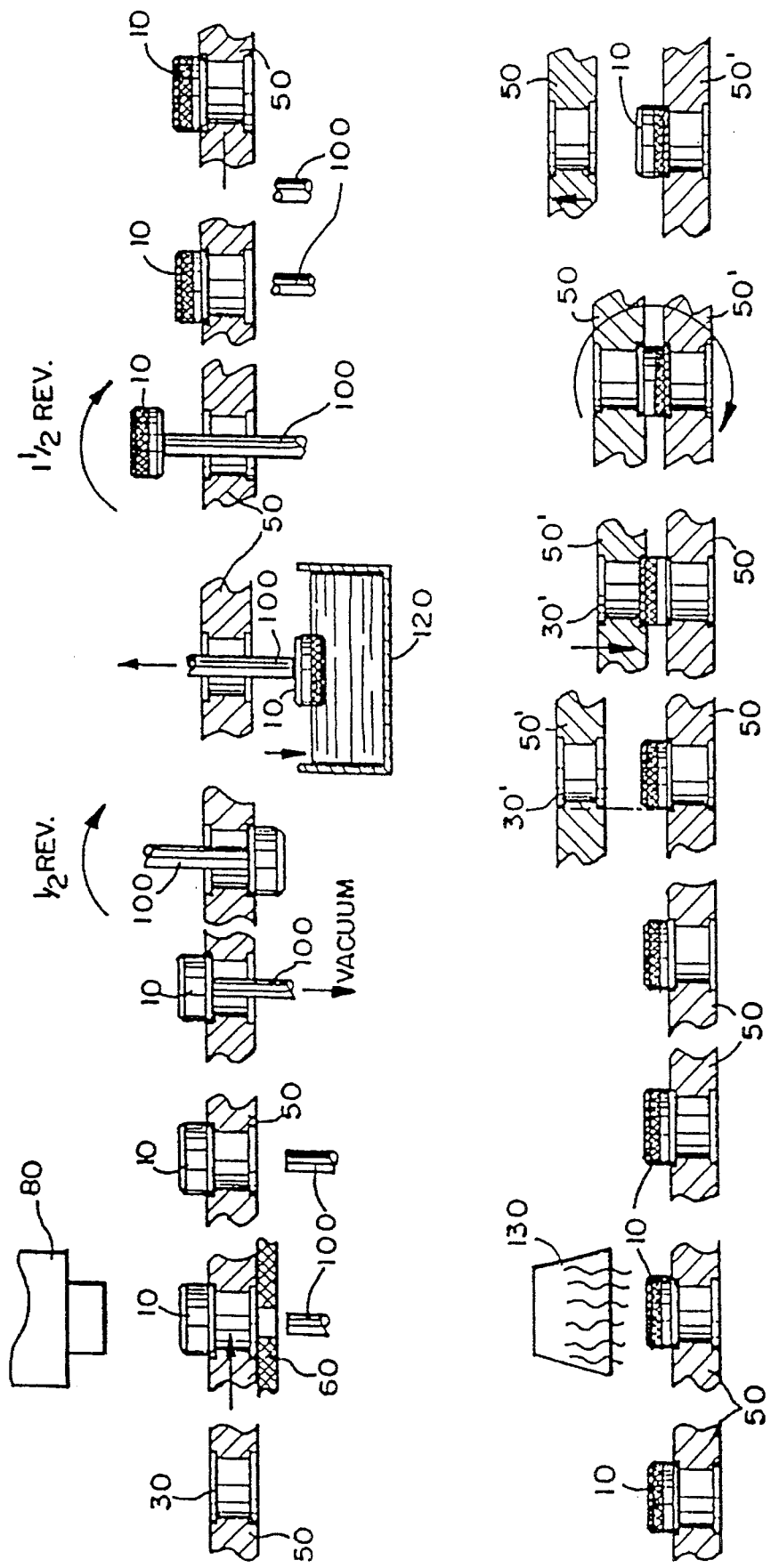
FIG. 5 is a partially diagrammatic, partially schematic representation of the steps of a preferred method for coating a tablet in accordance with the present invention.

As shown at the lower left portion of FIG. 5, once the individual products 10 have been released from the effect of the vacuum, the plate 50 bearing the partially coated individual products 10 may be moved into a dryer 130. Using conveyors or other conventional means, the plates are pushed into the dryer 130 and dried. After the coating has cured and the plates 50 have exited the dryer 130, a second plate 50' is moved into position such that the tablet holders 30' in the second plate 50' are in registry with the tablet holders 30 in the first plate 50, which contain the partially coated product 10. The second plate 50' is lowered toward the first plate 50 until the tablet holders 30' in the second plate 50' have engaged the product held in the first plate 50. Thus, as illustrated, the product 10 is "sandwiched" between the first and second plates 50,50'. The pair of plates 50,50' are then rotated one-half revolution, thereby reversing the relative positions of the first and second plates 50,50'. The first plate 50 is then raised, leaving the uncoated portion of the product 10 on the top, exposed, and the coated side on the bottom, i.e., within the tablet holder 30 of the plate 50'.

At this point, the preferred embodiment of the method illustrated has completely coated and cured a coating on about one-half of the product 10. It will be understood, however, that the above-described method may be repeated by transferring the plate 50' shown in the lower right section of the illustration to the upper left section, in other words, to the beginning of the process at the point immediately after the individual products 10 have been loaded into the plates 50. In this embodiment of the present invention, the above-described process is repeated and the remainder of the product 10 is coated. It should be further understood, however, that in any event, more or less than one-half of the tablet may be coated to provide different overall coating effects. For instance, if both "passes" coated less than one-half the height of the tablet, a band of uncoated product would remain exposed. On the other hand, if one or both of the "passes" were carried out to a depth substantially greater than one-half the height of the tablet, an overlapped "seam" appearance would be created.

Figure 6:
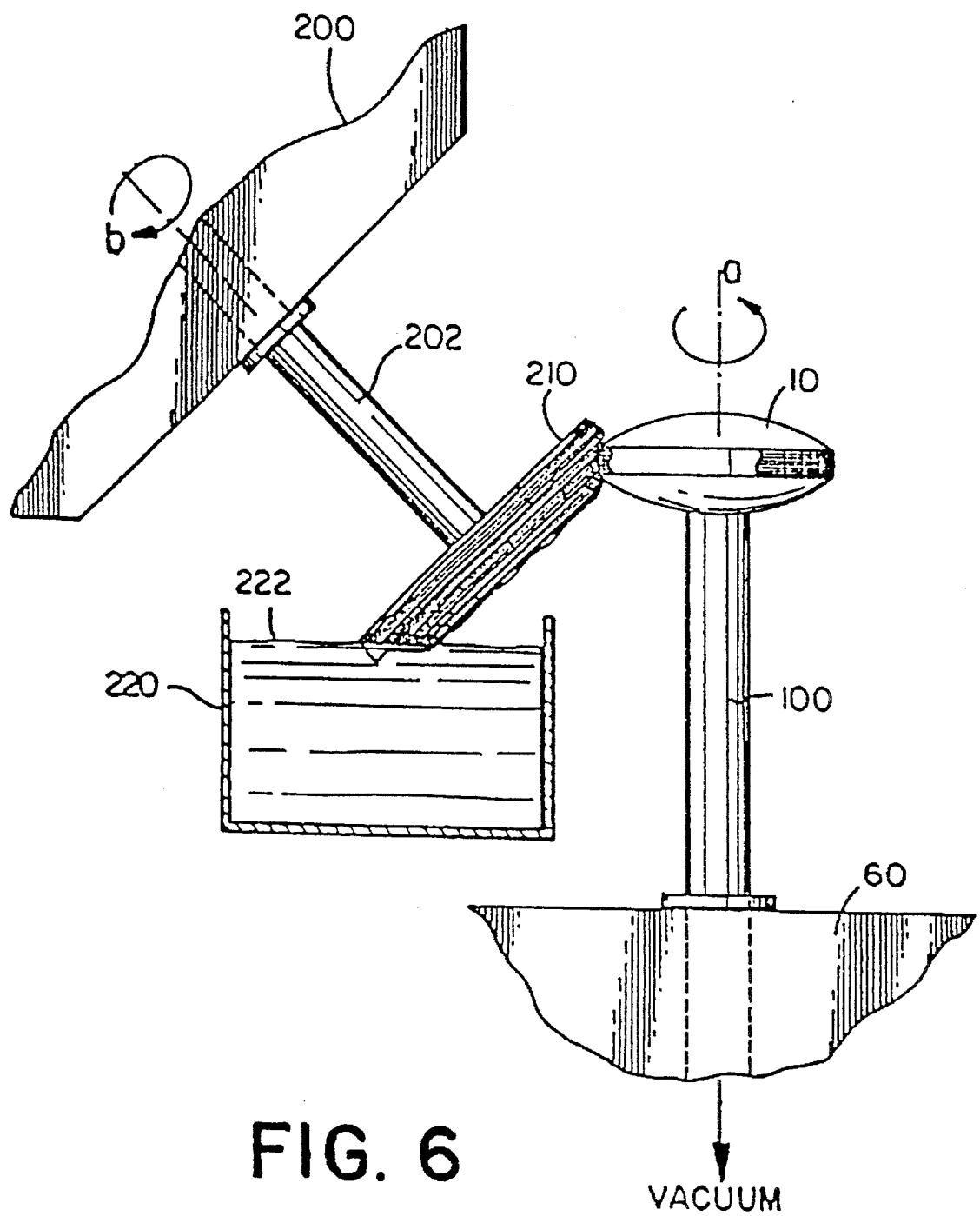
FIG. 6 is a broken away cross-sectional view of a portion of another embodiment of the present invention in which a band of coating material is applied to the products.

Referring now to FIG. 6, another feature of certain embodiments of the present invention is illustrated. In these embodiments, the vacuum tube 100 will be constructed such that it may be rotated about its longitudinal axis as shown by arrow a in FIG. 6. As understood by those of ordinary skill, such rotation may be accomplished using gear trains, belts and pulleys or other means for transferring rotational motion to a shaft. While rotating, the vacuum tube 100 is also acted upon by a source of vacuum, either the vacuum chamber 60 discussed above, or another source. The product 10 is thus firmly held in place upon the rotating vacuum tube 100 as shown. While the product 10 is rotating, it is brought into contact with a rotating wheel 210 or other application means for applying a coating. Preferably, the rotating wheel 210 provided is shaped and manipulated so as to come into close proximity with a portion of the product 10, such as the central "edge" shown. As the wheel 210 and product 10 rotate, the wheel 210 also passes through a quantity of coating material 222 and precisely coats a portion of the product 10. The wheel 210 rotates about a shaft 202 in the direction shown by arrow b and is mounted on a support structure 200 at an appropriate angle.

The present invention therefore also discloses methods whereby a relatively narrow stripe or band of coating material may be applied to a product. Most preferably, the product and the means for applying the coating rotate and are placed in close proximity. The means for applying the coating is preferably at least partially immersed in a quantity of coating material and passes therethrough while rotating. Using the embodiments illustrated in FIG. 6, it is possible not only to provide a different color "band" or stripe, but to also increase the thickness of the coating in a specified section, thereby creating the appearance of a seam or an overlapped gelatin capsule.

Figure 9:
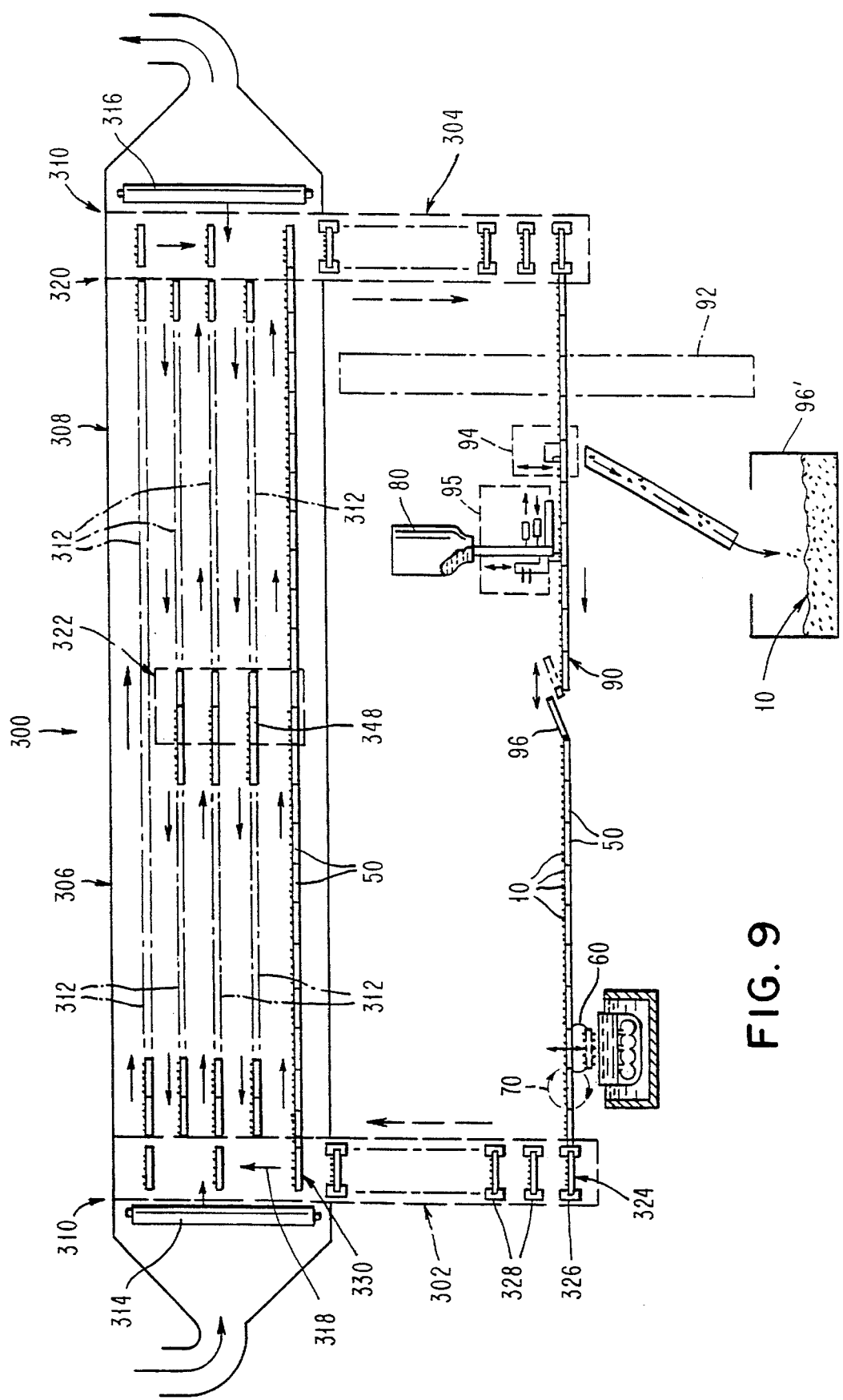
FIG. 9 is a diagrammatic representation of one embodiment of the apparatus of the present invention.

Referring now to FIG. 9, there is schematically shown a coating apparatus of the present invention which includes a separate rotating means 70 and an elevated dryer means 300. The dryer means 300 is shown positioned directly above the conveyor means 90 resulting in an efficient utilization of manufacturing space. A first elevator means 302 transfers plates 50 from the conveyor means 90 to the dryer means 300. After traversing the dryer means 300, a second elevator means 304 transfers the plates 50 from dryer means 300 to conveyor means 90, for further processing. Such further processing includes transfer means 92 which transfers the product to empty plate 50' and to a complementary coating apparatus having identical dipping, rotating and drying means for applying a second coating to the product. Unloading means 94 deposits coated products into a collection bin 96.

Dryer means 300 is comprised of a first section 306 through which the plates 50 are transported both horizontally and vertically upward, and a second section 308 through which the plates 50 are transported both horizontally and vertically downward. Means 310 for transporting the plates 50 through the dryer includes a plurality of vertically spaced guide means 312 along which the plates 50 are horizontally transported through the dryer. The transporting means 310 also includes horizontal transfer means 314 and 316 for transferring plates 50 from the elevator means 302 to the dryer means 300. Transfer means 314 transfer plates 50 from elevator means 302 to the first section 306, and transfer means 316 transfer plates 50 from elevator means 304 to the second section 308. Transporting means 310 also includes vertical transfer means 318 and 320 for transporting plates 50 vertically through the dryer 300. Vertical transfer means 318 transfer plates 50 between vertically spaced guide members 312 by transferring the plate to the next highest guide member 312. In a complementary manner, vertical transfer means 320 transfers plates 50 to the next lowest guide means 312. The dryer means 300 further includes mid-elevator means 322 interposed between the first section 306 and the second section 308. Mid-elevator means 322 transfer plates 50 upward between guide means 312 in the first section 306 and downward between guide means 312 in the second section 308.

After each plate 50 is processed by the dipping and rotating stations, the plates are advanced into elevator means 302 and transferred vertically to dryer 300. In a preferred embodiment of the invention, a first incremental advancement means 95 is provided for precise loading of tablets by the feeder apparatus 80 and a second incremental advancement means 96 is provided to advance the plates through the processing stations. As each plate 50 moves beneath the feeder apparatus, a row of product is correctly positioned and inserted into spaces within the plate 50. The advancement of each plate 50 also advances the plates which have been filled. Thus, by pushing the leading edge of a first plate against the trailing edge of the plate in front of it, the need for a motive force to move the plates along the conveyor is eliminated. The incremental length of each advance by advancement means 95 is equal to the pitch between rows of product. However, the rate of advance by advancement means 96 is increased after a plate has been filled. As illustrated, after three plates are full, one plate is advanced at a greater pitch length as shown, which is equal to the width of a plate. By increasing the incremental length of the advancement of the plates, timing advantages are obtained which increase the overall efficiency of the production cycle. It should be noted that after the increment has been increased, the plates are again in close-spaced relation so as to urge against one another. As before, this eliminates the need for further sources of motive force to move the plates through the apparatus.

As is illustrated in FIG. 9, the plates 50 are advanced from conveyor means 90 into a plate entry station 324 of elevator 302. Plate entry station 324 is contiguous with conveyor 90 so that the advancement means 96 will cause plates 50 to be moved into entry station 324. Upon being moved into the entry station 324, the plates 50 are grabbed by an engagement means 326 which engage the side edges of plates 50. The plates 50 are then raised incrementally by a plurality of engagement means 326 through a series of intermediate plate retaining means 328 until exit station 330 is reached. Several embodiments for raising the plates 50 through the entry, intermediate and exit stations will be described in more detail below with reference to FIGS. 13 through 17.

Figure 10:
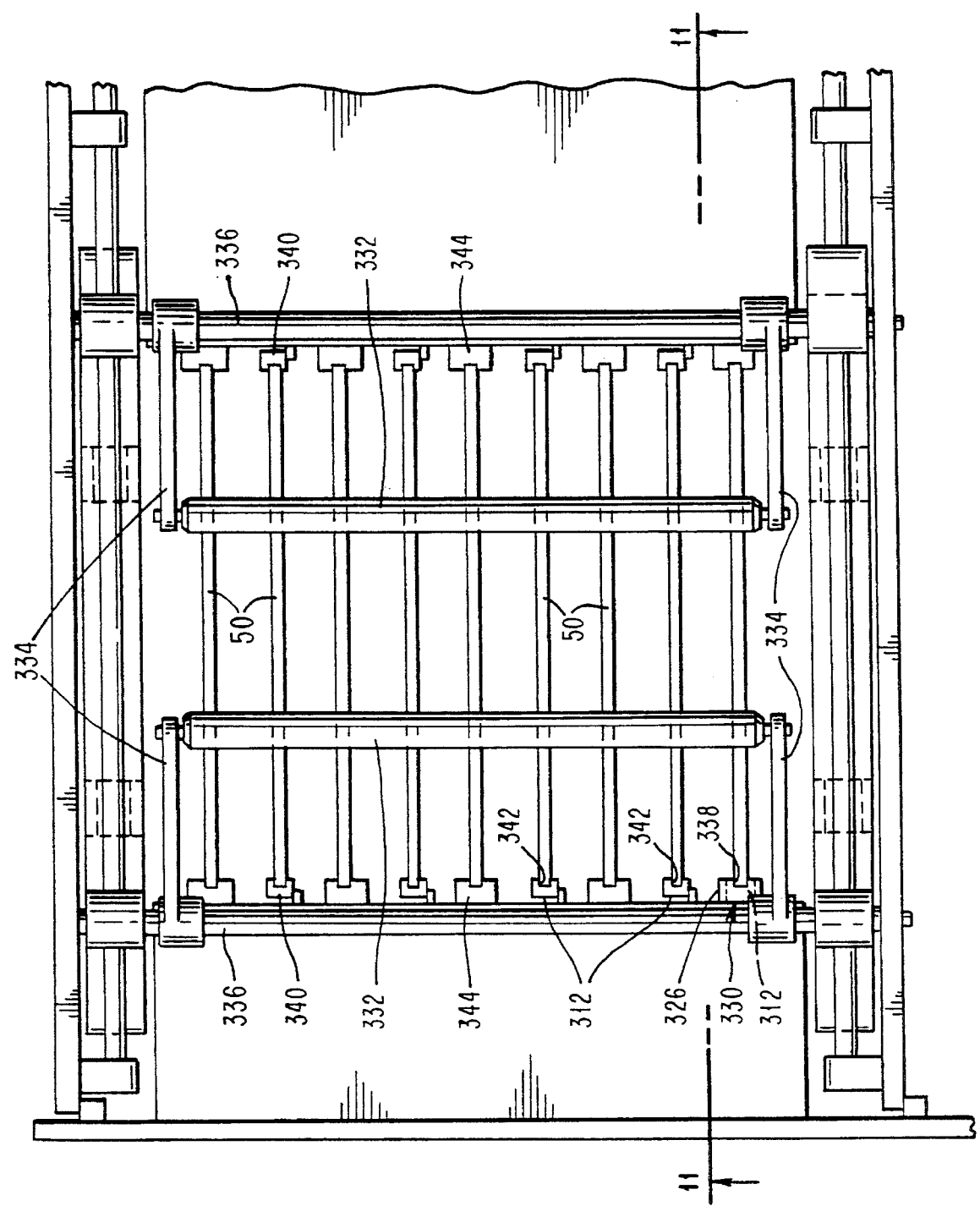
FIG. 10 is an elevational view of one embodiment of the transfer means of the apparatus of the present invention.

After each plate 50 reaches the exit station 330, transfer means 314 transfers the plate into dryer means 300. FIG. 10 shows one embodiment of the transfer means 314. In the embodiment shown in FIG. 10, transfer means 314 includes a pair of pusher bars 332 that contact longitudinal side edges of plates 50 and push the plates 50 into the drive means 300. The pusher bars 332 are rotatably secured to articulating arms 334 which are mounted to a rotating shaft 336.

Pusher bars 332 are maintained in a first position prior to a push stroke. A plate 50 is received in the exit station 330. At this station, the engagement means 326 is aligned with the lower most guide means 312 (blocked from view by means 326). The engagement means 326 is a channel block in which the channel 338 is adapted to engage side edges of a plate 50 in such a manner to allow the plates to slide within the channel. Guide means 312 is similarly comprised of a channel block 340 having a channel 342 for engaging side edges of plates 50 while also allowing the plates 50 to slide within the channel. It should be noted that FIG. 10 also shows channel blocks 344 which comprise the vertical transfer means 318 for transferring plates to the next highest guide means 312. In the illustrative embodiment shown in FIG. 10, there are nine levels of the vertically spaced guide means 312 with four of the channel blocks 340 being visible and five being obscured by the channel blocks 344 and channel block 326 at exit station 330.

Figure 11:
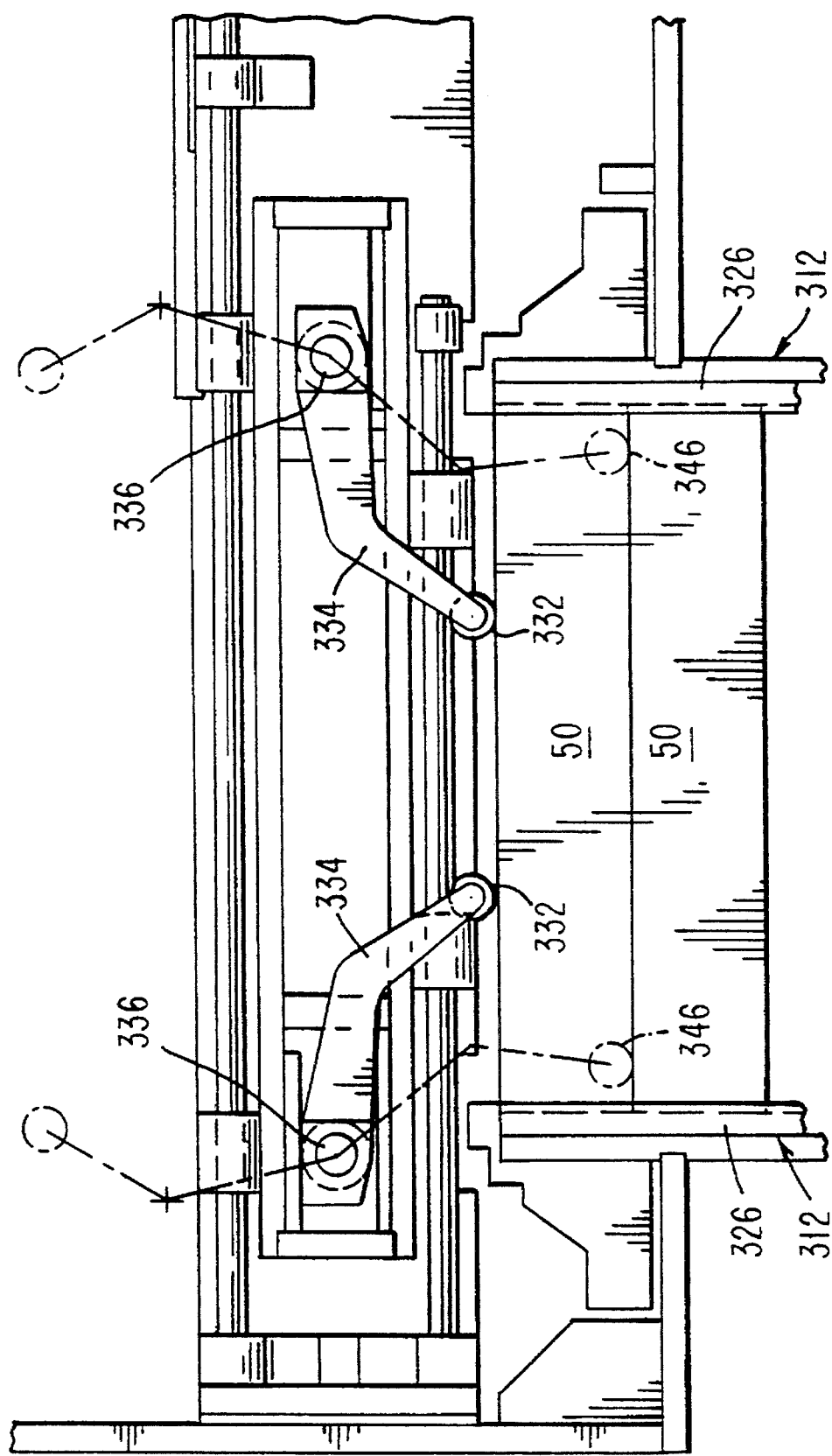
FIG. 11 is a plan view taken along lines 11—11 of FIG. 10.

Referring now to FIG. 11, the pusher bars 332 are moved from the dwell position shown in FIG. 11 to the full push stroke position shown in phantom at 346. The action of this stroke of the pusher bar 332 causes the plate 50 to slide from the exit station 330 into the guide means 312 of dryer 300. As can be seen in FIG. 10, not only is the plate 50 in the exit station 330 pushed into the dryer, but also plates 50 that are positioned in channel blocks 344 were also pushed into the dryer by the stroke motion of pusher bars 332.

Returning to FIG. 9, horizontal transfer means 314 and 316 are identical and the pusher bars are programmed to work in a complementary manner so that when pusher bars of means 314 are in dwell, the pusher bars of means 316 are in motion and vice versa. A full description of the manner in which the plates 50 traverse sections 306 and 308 of the dryer 300 will now be described.

Referring to FIG. 10, the channel blocks 344 are adapted to be shifted from the positions shown in FIG. 10 to a position aligned with the next lowest guide means of channel bar 340. Similarly, channel engagement means 326 is shifted from the exit station 330 to a lower position not shown for receiving the next plate 50 to be introduced into the dryer. A more detailed description of several embodiments for the engagement means 326 and channel blocks 344 and for moving these engagement means will be described below in connection with FIGS. 13 to 17. The positions of channel blocks 344 shown in FIG. 10 is positioned in which a plate 50 is engaged in the blocks and is ready to be transferred into the dryer upon the push stroke motion of the pusher bars 332. After the plates have been pushed out of the channel blocks 344 and entry block 326, the pusher bars return to the dwell position and the channel blocks 344 and 326 are moved down one level to be in position to receive another plate 50.

As mentioned above, mid-elevator 322 operates together with vertical transfer means 318 to move plates 50 upward in section 306. In addition, mid-elevator 322 operates together with vertical transfer means 320 to move plates 50 downward in section 308. The mid-elevator 322 is comprised of a series of vertically spaced pairs of guide means 348. Each pair of guide means 348 is connected to a actuating means, which will be described in more detail below, that moves each pair of mid-elevator guide means 48 up and down between two levels of dryer guide means 312. The movement of the pairs of guide means 348 is identical to the up and down movement of the channel blocks 344.

The sequence of operation for the movement of the plates 50 within the dryer 300 is best described in reference to the drawings shown in FIGS. 12(a)–12(e). To transport the plates 50 through the dryer 300, there are five separate motion devices that are coordinated to control movement of the plates 50. These systems are horizontal transfer means 314 on the extreme left hand side of the dryer 300 and horizontal transfer means 316 on the extreme right hand side of the dryer 300. Each of these means has a dwell position in which the pusher bars 332 are fully retracted and a stroke position in which the pusher bars are fully extended. The plate movement means further includes vertical transfer means 318 located on the extreme left hand side of the dryer 300 and vertical transfer means 320 located on the extreme right hand side of the dryer 300. Means 318 and 320 both have two positions, an up position in which the engagement means are aligned with the higher of two levels of guide means 312 and a down position in which the engagement means aligned with the lower of two adjacent guide means 312. Also included is mid-elevator guide means 348 which also has similar up and down positions to means 318 and 320.

Figure 12A:
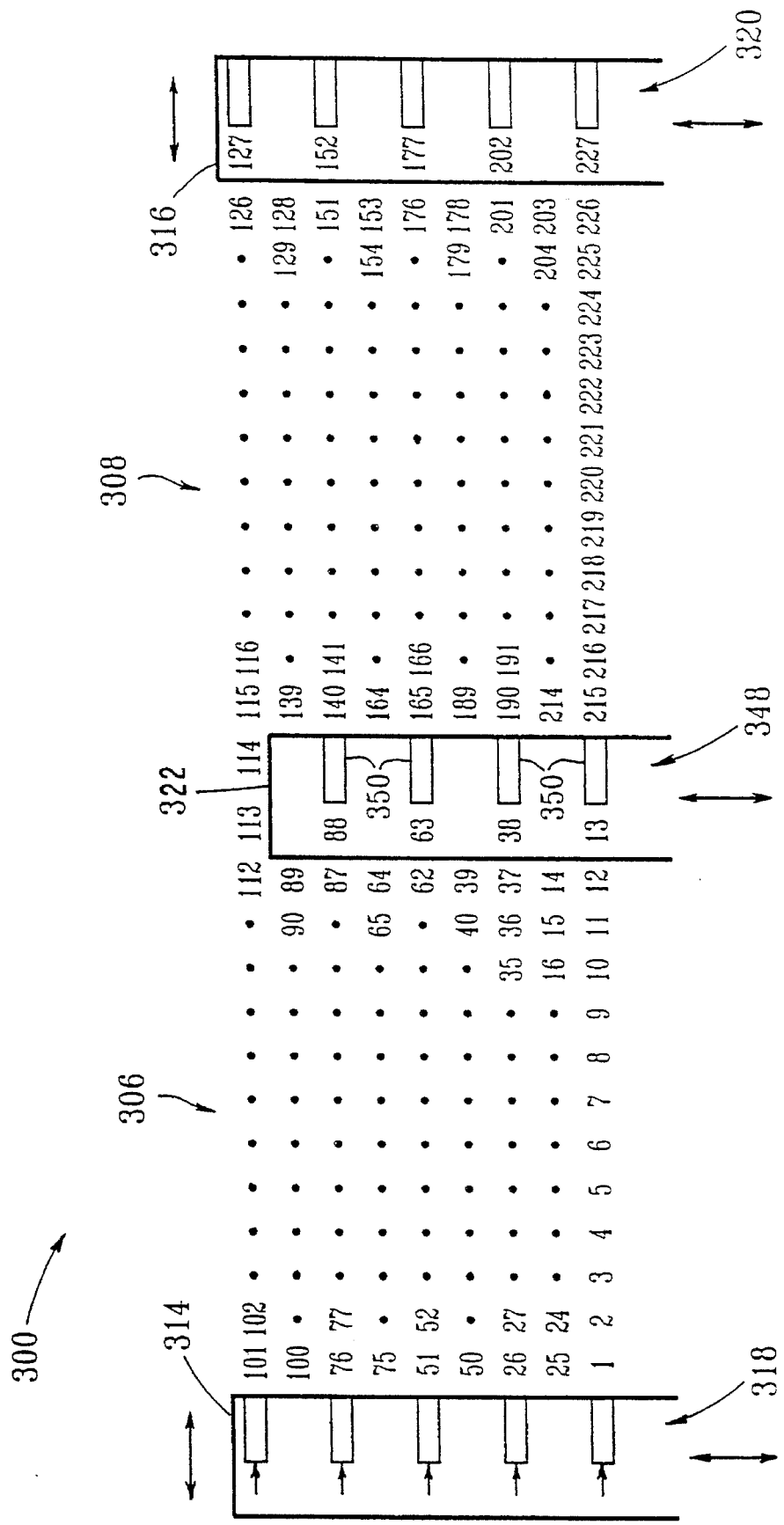

As shown in FIG. 12(a), vertical transfer means 318, 320 and mid-elevator guide means 348 are all in the down position. Horizontal transfer means 314 is in the full stroke extended position in which plates 50 have been transferred into the dryer 300. In order to illustrate the sequence of movement, plates have been numbered in order to show their relative movement throughout the sequence. Plates 1, 26, 51, 76 and 101 were previously positioned in the vertical transfer means 318 and have now been transferred into the dryer 300. In the mid-elevator 322, in each pair of guide means 348 there is positioned one empty plate 350. The empty plates 350 shift back and forth between the left and right sides of the mid-elevator, with all the plates 350 always being on the same side. The stroke of transfer means 314 causes plates 13, 38, 63 and 88 to be transferred into mid-elevator 322 which causes empty plates 350 to be shifted from the left side to the right side. In order to accomplish the transfer of plates from section 306 to 308, there is a top row of guide means 312 which allows plates 50 to transfer all the way across the dryer from means 318 to means 320 without entry into the mid-elevator 322. As can be seen in FIG. 12(a), upon the stroke of means 314, plates 113, 114 and 115 have moved along the top guide means above the mid-elevator 322. Also upon the push stroke of means 314, plates 227, 202, 177, 152 and 127 are transferred from dryer section 308 onto transfer means 320. The guide means 312 are similar to conveyor 90 in that the movement of the plates therein is caused only by the action of leading edge of a plate pushing against the trailing edge of the next plate. No other motive force is needed except for the action of the pusher bars.

Figure 12B:
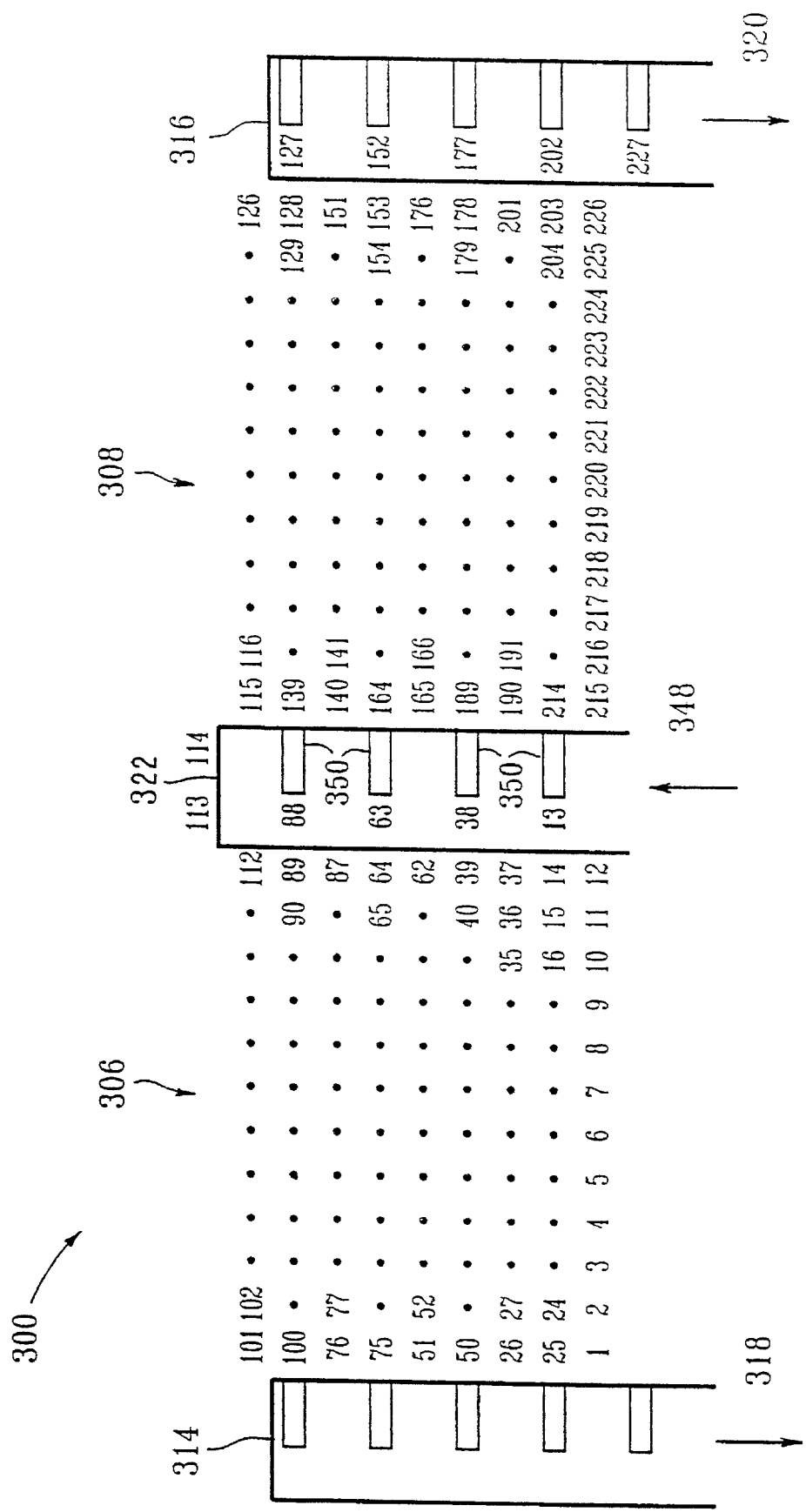

As shown in FIG. 12(b), in the next timing period, vertical transfer means 318 and 320 shift down one level of guide means 312 and mid-elevator 322 transfer means shifts up one level. Transfer means 318, being cleared of plates, is shifted down to be ready to receive the next group of plates. Transfer means 320 shifts to align its load of plates with the next lowest guide means level. In addition, plate 227 is shifted down into elevator 304 for transfer to conveyor 90. The movement of the mid-elevator aligns the plates on its left side with next highest level of guide means.

Figure 12C:
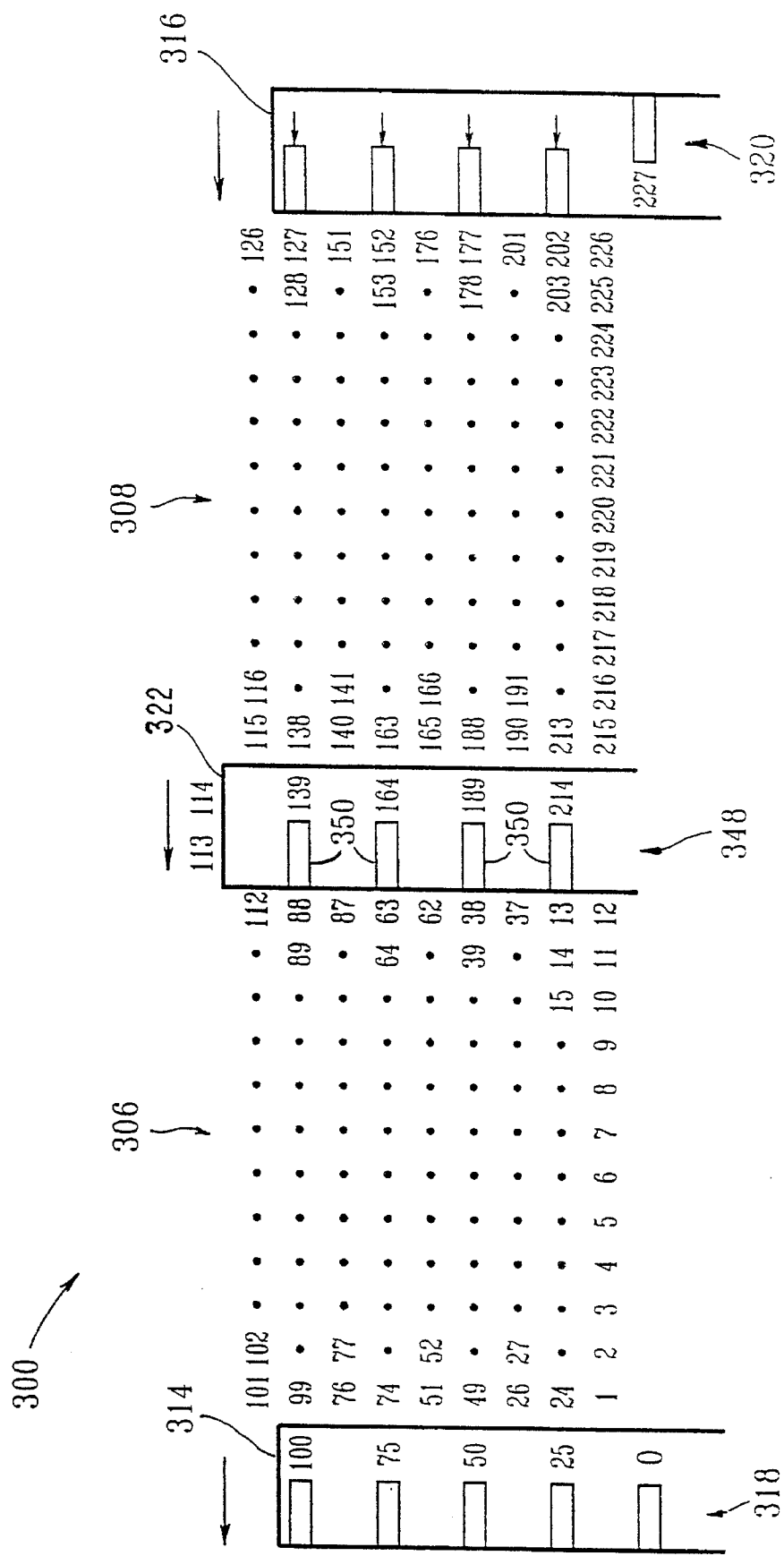

As shown in FIG. 12(c), horizontal transfer means 316 extends a full stroke to the left which causes plates 127,152, 177 and 202 to be transferred into dryer section 308. In addition, plates 139,164, 189 and 214 are transferred into the mid-elevator 322. Empty plates 350 are shifted to the left side causing plates 13, 38, 63 and 88 to be transferred into dryer section 306. Also, plates 25, 50, 75 and 100 are transferred into transfer means 318.

As shown in FIG. 12(d), transfer means 318 and 320 shift up one level while mid-elevator 322 shifts down one level. Transfer means 318 aligns its plates with the next highest level of guide means 312 and also aligns the next plate from elevator means 302 with the bottom level of guide means 312. The plates in the mid-elevator 322 are aligned with the next lower guide means level. The empty transfer means 320 is aligned with the next highest level to receive the next series of plates to be lowered.

Figure 12E:
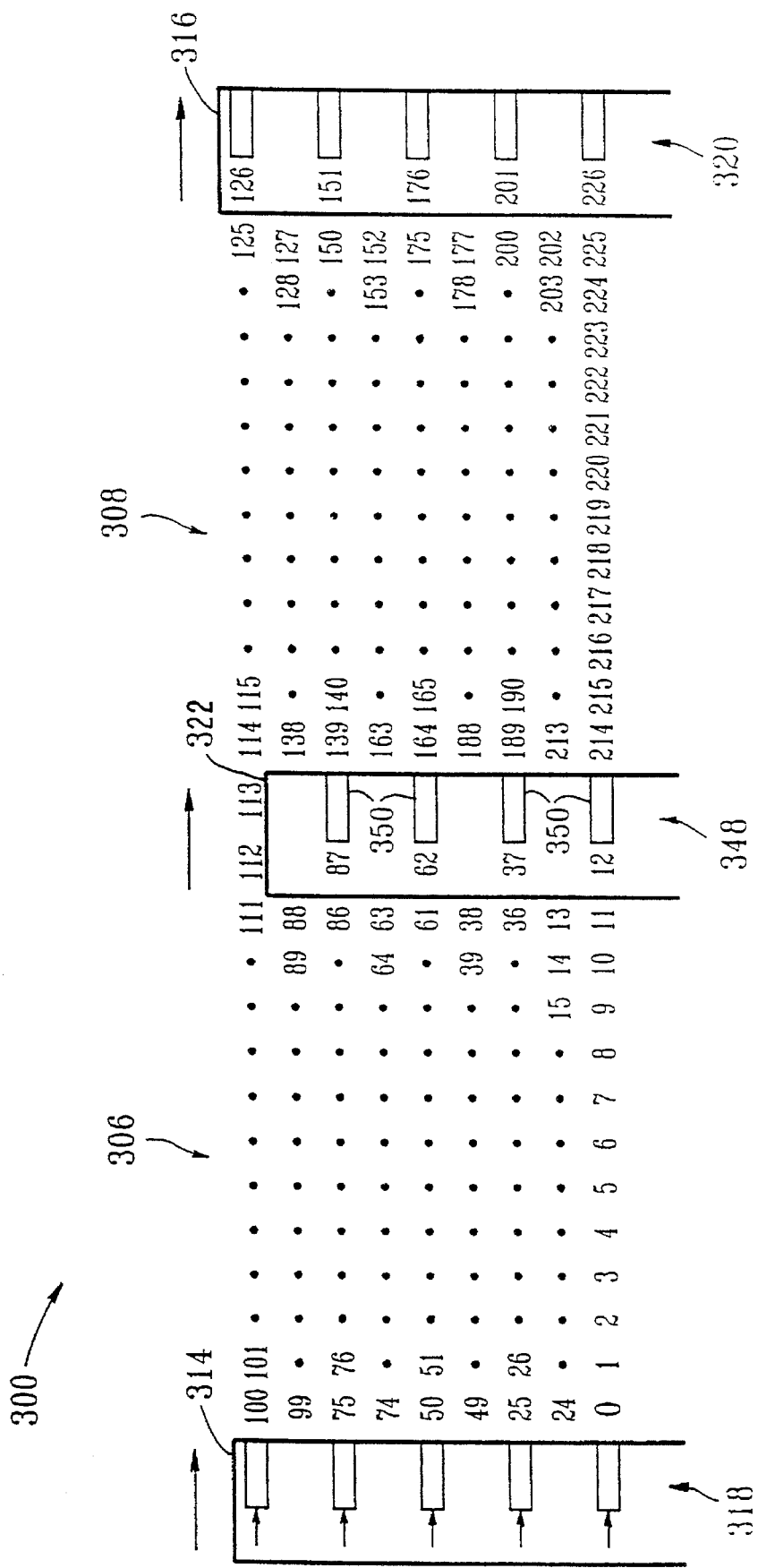

As shown in FIG. 12(e), transfer means 314 is extended to the right to a full push stroke to transfer plates 25, 50, 75 and 100 into dryer 300 along with the next plate 0 transferred from elevator 302. Plates 12, 37, 62 and 87 are shifted into mid-elevator 348. In addition, plates 126, 151, 176, 201 and 226 are shifted into transfer means 320. Also, the plates on the top row are all shifted to the right. Thus, as can be seen, the plates initially traverse horizontally and vertically upward through section 306 and then horizontally and downward through section 308 of dryer 300. During the entire time that the plates traverse through dryer 300, hot air is passed through the dryer in order to set the coating on the tablets. This unique dryer system provides a sufficient drying time while utilizing efficient manufacturing space and timing for a continuous mass production apparatus for coating large numbers of tablets or other forms of products to be coated.

Figure 13A:
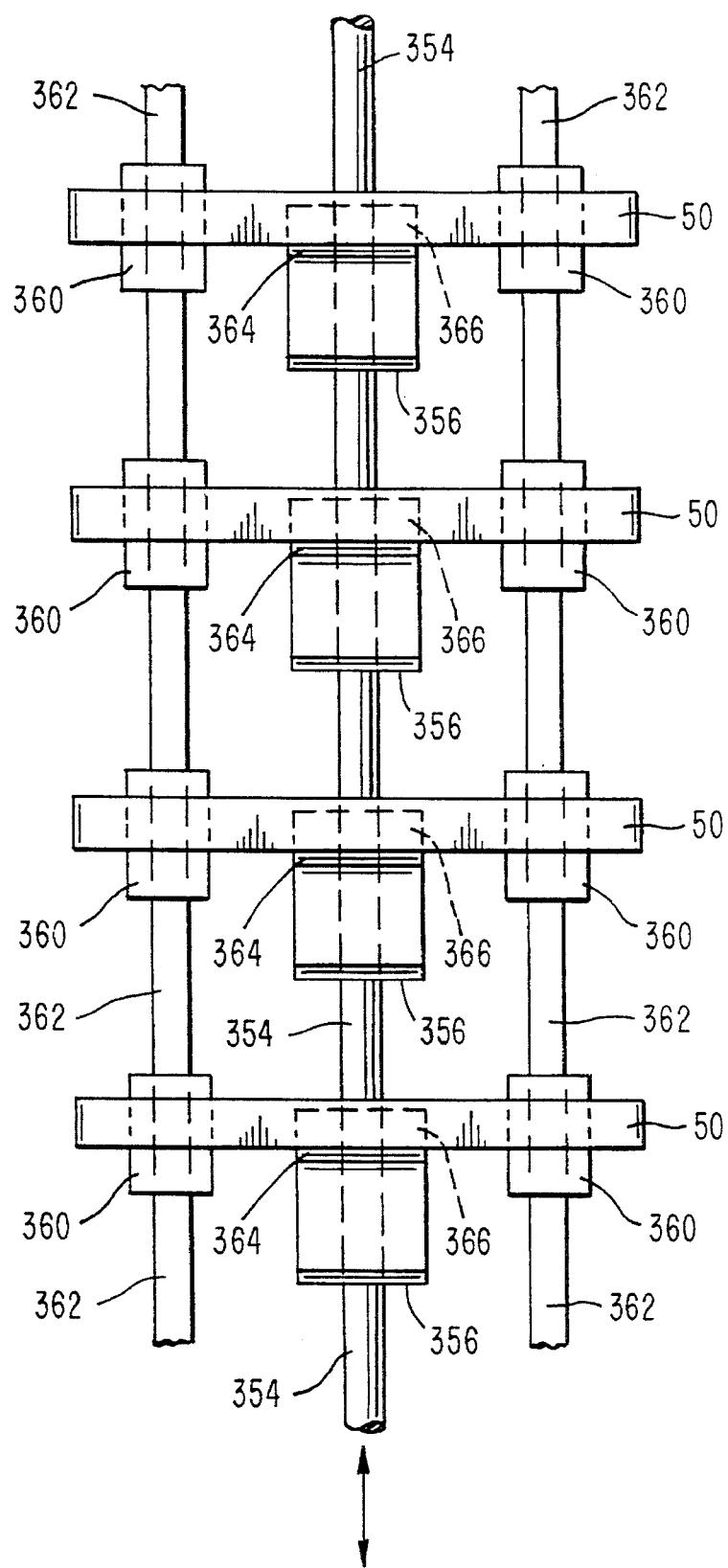
FIGS. 13(a)–13(c) are elevational and partial cross-sectional views of one embodiment of the elevator of the present invention.
Figure 13B:
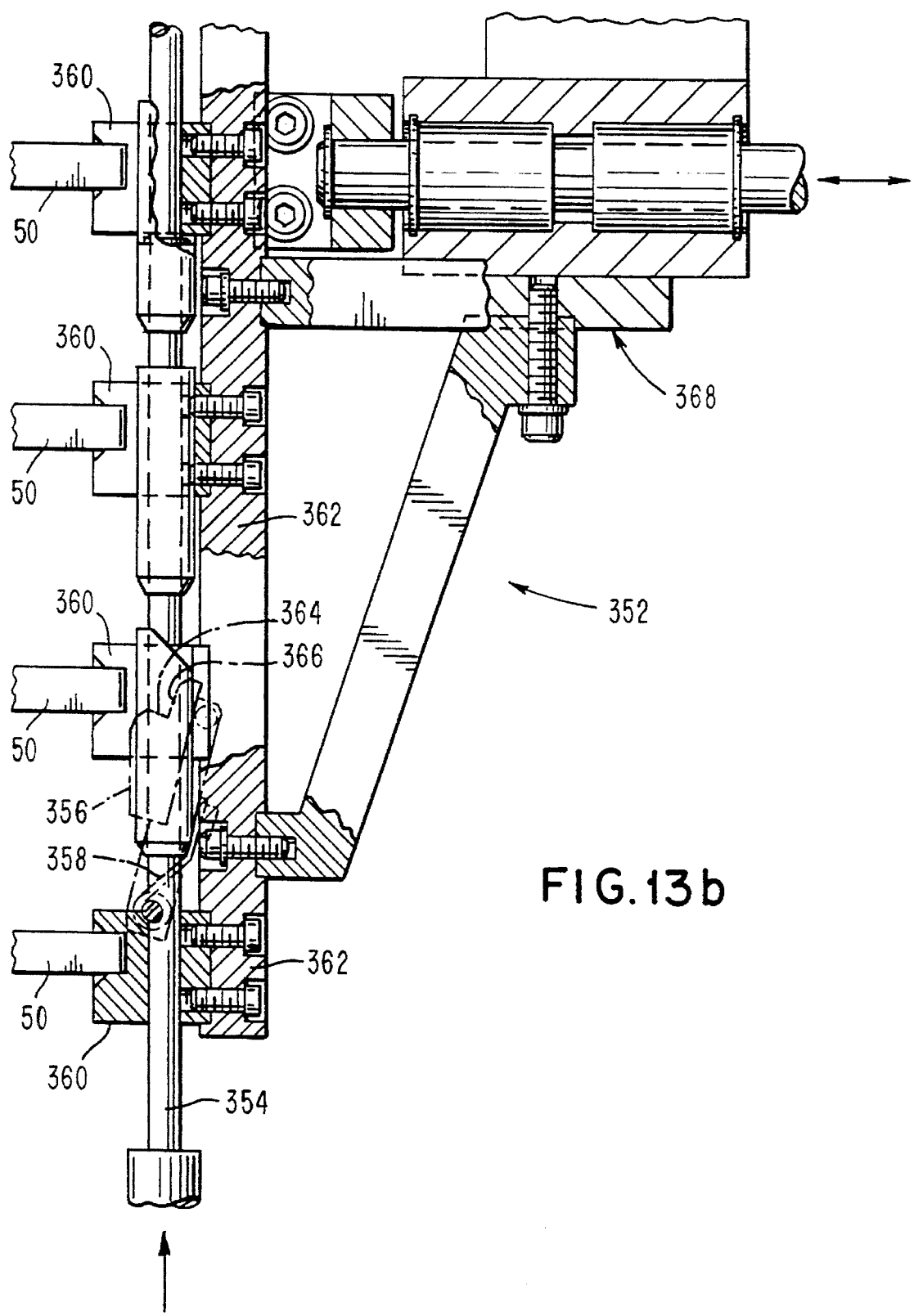

Elevator means 302 and 304 may take any suitable form and structure in order to transfer plates 50 from conveyor 90 to overhead dryer 300. Although a description of the operation of various embodiments for the elevator means 302 will be provided it should be understood that for each embodiment the means 304 will operate identically except that the plates will be lowered instead of being raised. FIGS. 13(a) and 13(b) show one embodiment in which the elevator means is in the form of a lift bar means 352. The lift bar means 352 of the present invention includes an elongated lift bar 354 having attached thereto a plurality of vertically spaced retaining bars 356. The retaining bars 356 are secured to the lift bar 354 by a spring means 358. A plurality of channel means 360 are secured to connection member 362. The channel means 360 are adapted to retain the side edge of plate means 50 and in the embodiment shown in FIGS. 13(a) and 13(b), a pair of channel means 360 are used for each side edge of the plate 50.

In operation, a plate means 50 enters the elevator 302 from conveyor 90 and is engaged by the lowermost channel means 360 on the opposed side edges of each of the plate 50. The plate 50 is also engaged by the retaining bar 356. The plate 50 rests on ledge 364 and against flange 366. The lift bar 354 is caused to move vertically a distance sufficient to transfer each plate 50 to the next highest channel means 360. In order to allow the lifting process to occur, the channel means 360 are moved away from the plate to no longer engage the plates. Means 368 is adapted to shift the connecting member 362 between engaged and non-engaged positions. After the lift bar moves upward, the means 368 causes the channel means 360 to re-engage the plates 50. The lift bar 354 is then moved downward to return each of the retaining bars 356 to its initial position engaging the next plate 50 ready to be transferred upward. The spring means 358 allows the retaining bar to pivot back as the bar 356 contacts and passes the next plate 50 and to pivot forward to engage that plate on the ledge 366 after clearing the plate. The mechanism for moving the lift bar 354 and the channel connection member 362 includes a mechanical cam and operates by conventional drive means.

Figure 13C:
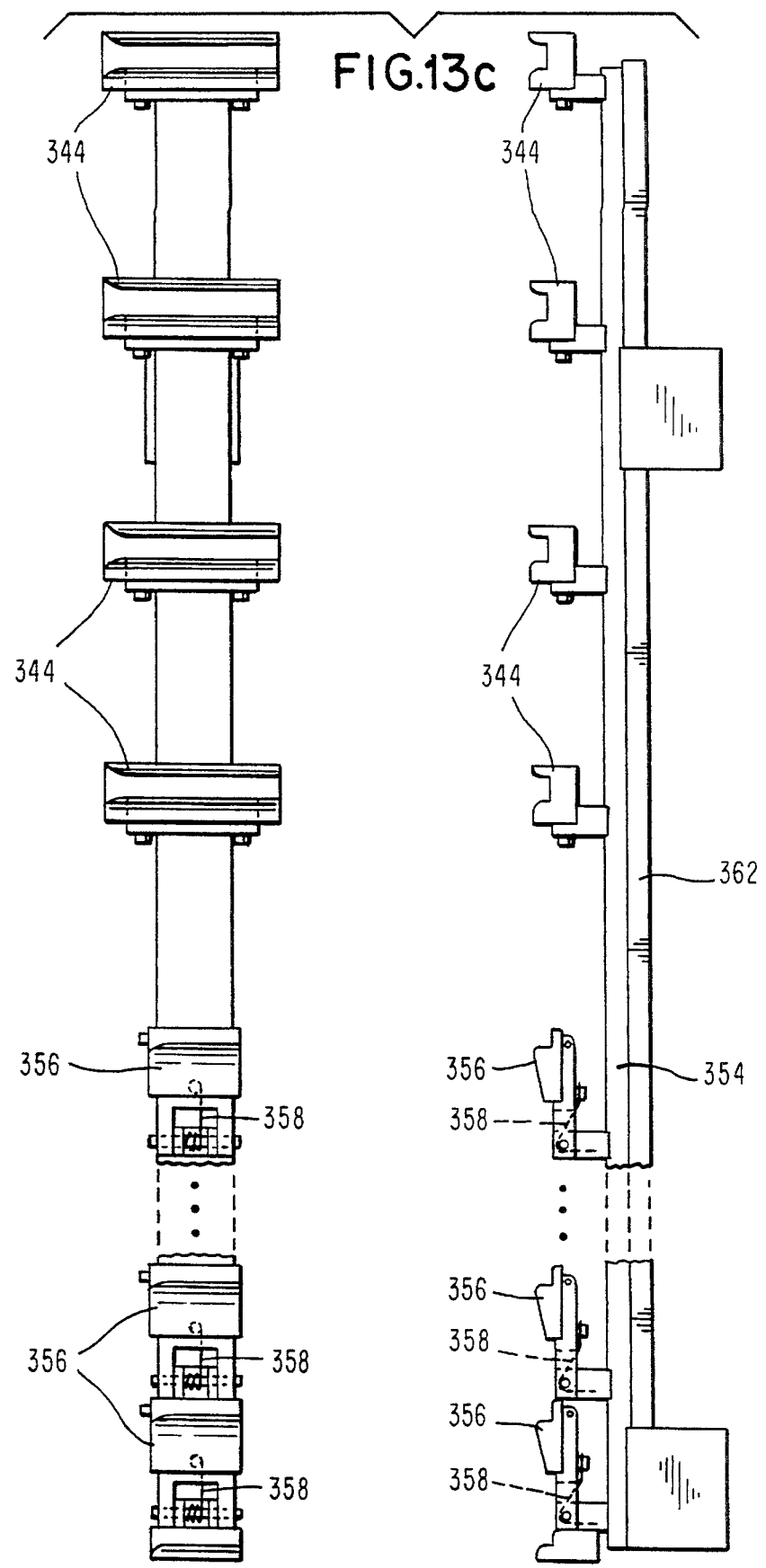

FIG. 13(c) shows the lift bar 354 and the retaining bars 356 and the channel blocks 344 of the vertical transfer means 318, 320 for the dryer 300. The channel blocks 344 are also secured to the lift bar 354 which as stated moves up and down between two positions. There is no need for the channel blocks 344 to have the pivoting feature because the plates are transferred out of the channels by the horizontal transfer means 314, 316.

Figure 14A:
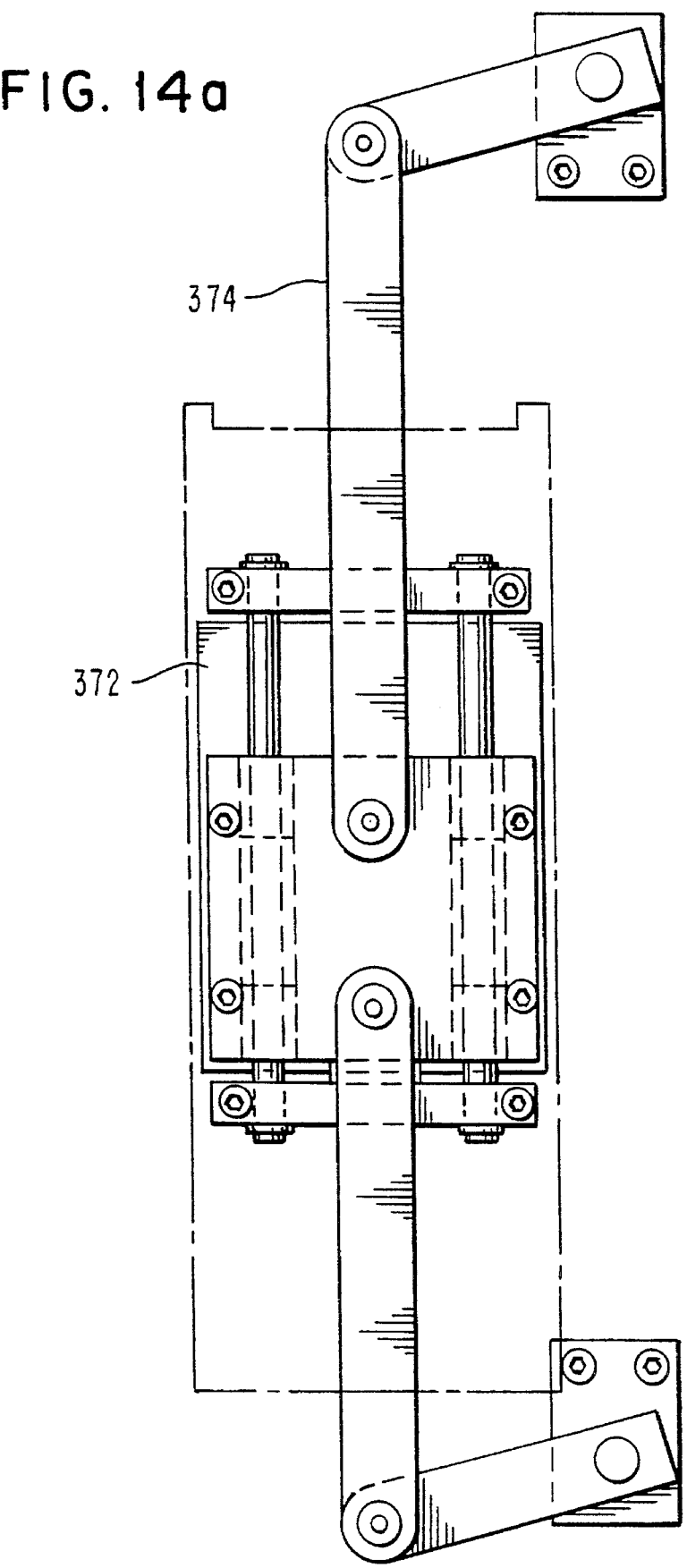
FIG. 14(a) is an elevational view of one embodiment of the dryer mid-elevator of the apparatus of the present invention.
Figure 14B:
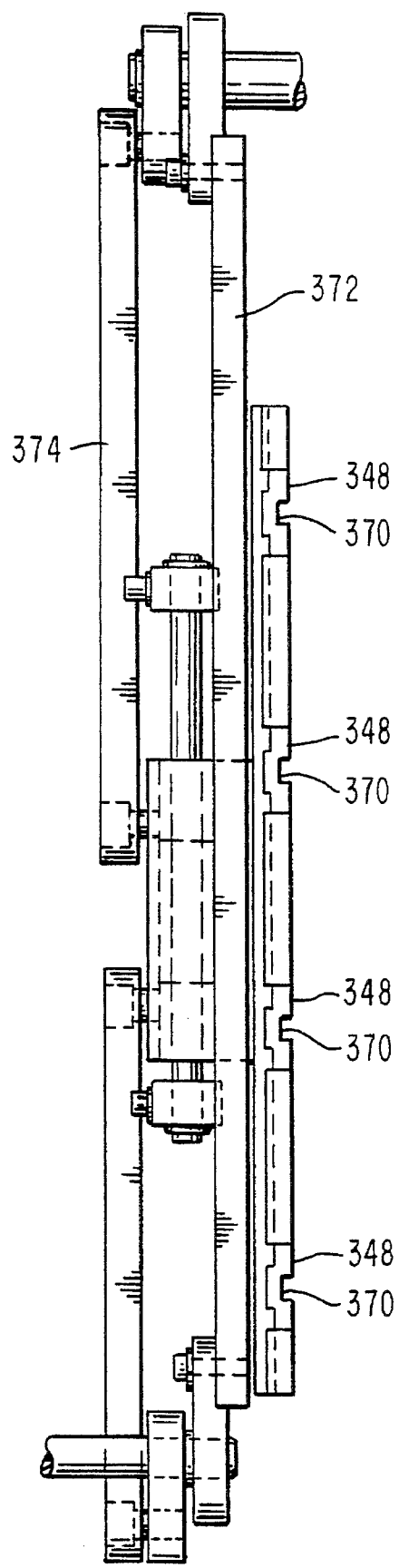
FIG. 14(b) is a broken away, side elevational view of the dryer mid-elevator of FIG. 14(a).

FIGS. 14(a) and 14(b) show an illustrative embodiment of mid-elevator 322. FIG. 14(b) shows the plurality of guide means 348 each having a channel 370 for receiving a plate 50. The guide means 348 are mounted to a plate 372. The plate 372 is moved up and down and hence the guide means 348 are moved up and down by linkage means 374.

Figure 15:
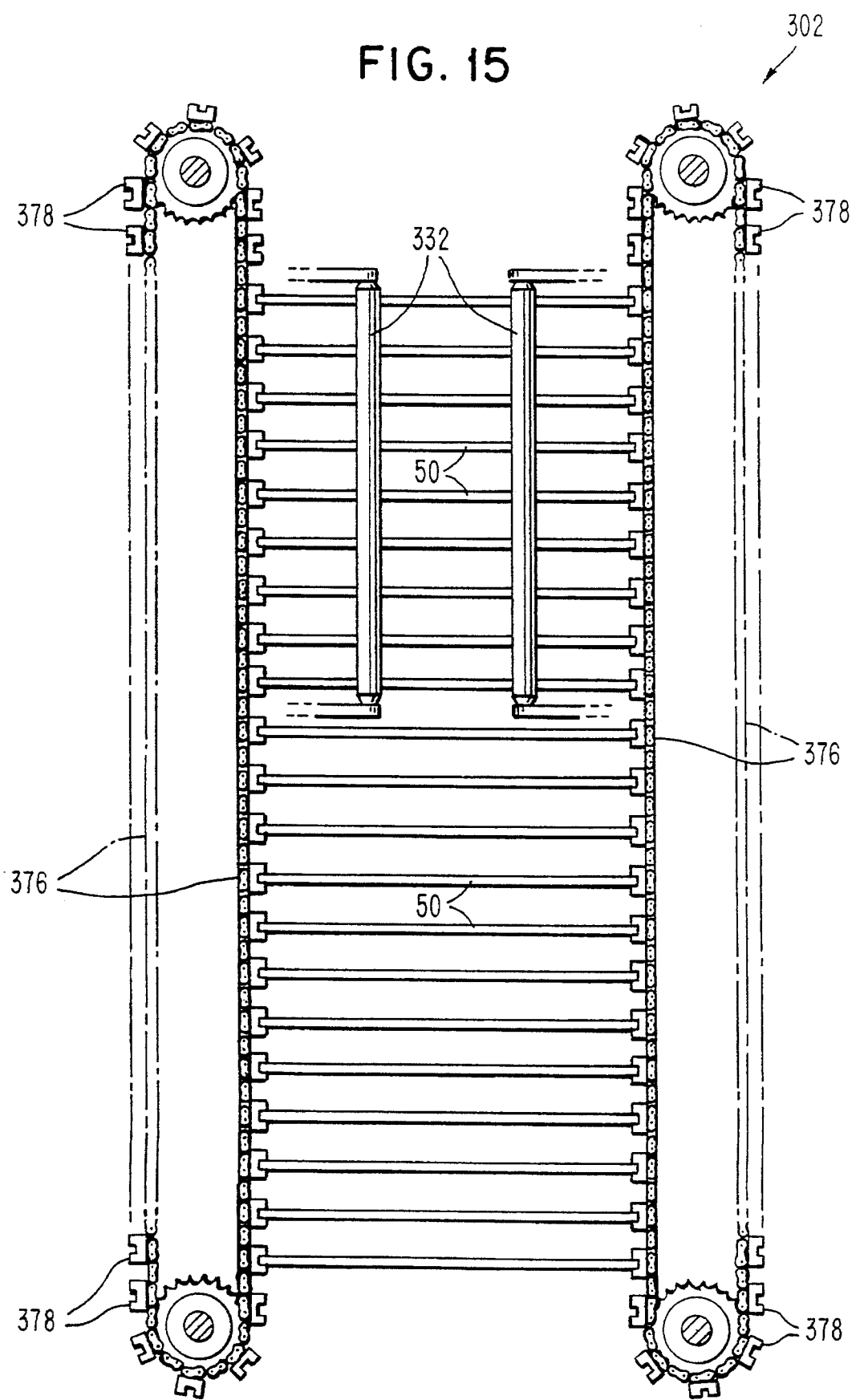
FIG. 15 is an elevational view of another embodiment of the elevator of the present invention.

FIG. 15 is an alternative embodiment for elevators 302 and 304 in which the drive means is in the form of a continuous chain means for lifting the plates 50 from the conveyor 90 up to the dryer 300 and vice versa. As shown in FIG. 15, elevator means 302 includes a pair of chains 376 having mounted thereto a plurality of engagement means 378. Sprockets 380 are intermittently rotated to continually move the engagement means 378 into positions to transfer the plates 50 upward/downward. In this embodiment, the chain means acts as both the elevator for transferring plates from the conveyor to the dryer and as the vertical transfer means for transferring means between the vertically spaced guide means in the dryer. Pusher bars 332 are shown for transferring the plates 50 into the dryer.

Figure 16:
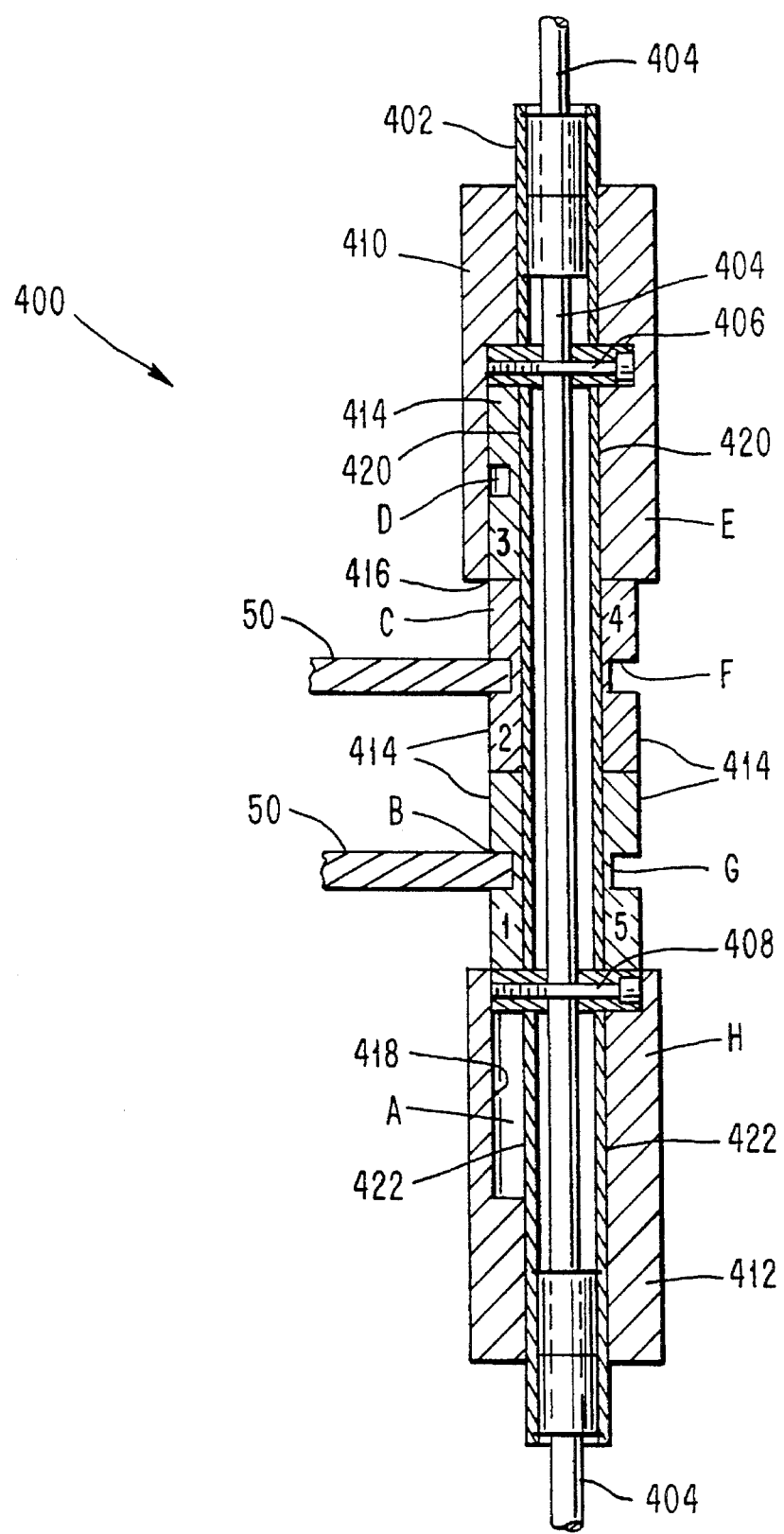
FIGS. 16 is an elevational view of a third embodiment of the elevator of the present invention.

FIG. 16 shows yet another embodiment for the elevator means and vertical transfer means. The embodiment of FIG. 16 is a lift rod mechanism. The lift rod mechanism 400 includes a tubular guide 402 which is hollow and contains therein rod 404. Rod 404 is adapted to reciprocate up and down within tubular guide 402. A conventional cam driven system moves the rod up and down between two positions. Also connected to rod 404 is a drive mechanism for selectively rotating the rod 180° at a time. A conventional index drive mechanism is utilized in order to rotate the rod 180°. Attached to rod 404 is an upper pin 406 and a lower pin 408. Pin 406 is located within an upper transfer unit 410 and pin 408 is located within a lower transfer unit 412. Tubular guide 402 is adapted to receive and guide a plurality of channel blocks 414 on opposite sides of the tube 402. The channel blocks 414 are advanced upward on one side and downward on the opposite side by pushing the blocks one against the other within the guides in tube 402. For ease of description only FIG. 16 shows only a two channel block spacing between the upper unit 410 and lower unit 412. However, it should be understood that in actual practice, the lift rod mechanism 400 will have many more channel blocks located between the upper and lower transfer units. The upper transfer unit 410 includes an open compartment 416 for receiving a channel block 414 and transfer unit 412 includes open compartment 418 for receiving a channel block 414. Pin 406 is located at the extreme upper portion of compartment 416 and extends through a pair of slots 420 in tube 402. Also as shown in FIG. 16, pin 408 is located at the upper most position within the compartment 418 and extends in a pair of slots 422 in tube 402.

To describe the operation of the lift rod mechanism 400, the eight positions which can contain channel blocks 414 have been assigned a letter (A)–(H). It should be understood that position (B) is the first position in the elevator in which a plate 50 is transferred from the conveyor in each coating section. It should also be understood that position (C) represents a position aligned with the uppermost elevator guide means 312. As shown in FIG. 16, the transfer units 410 and 412 are positioned such that compartments 416 and 418 are aligned with channel blocks facing the inside of the apparatus that contain plates 50 being lifted. For each elevator, there is a mechanism 400 engaging opposite sides of the plates 50. Also for the purpose of description only, the channel blocks shown in FIG. 16 have been labelled 1–5 in order to describe their movement throughout the mechanism. As shown in FIG. 16, block 3 is located in compartment 416. Block 3 was moved into compartment 416 by the movement of rod 404 upward the height of the compartment 416 and the pin 408 pushing the blocks 1, 2, 3 upward within the guide in tube 402. During this movement, the tube remains stationary and the pins 408 and 406 ride within slots 420 and 422. Rod 404 then is rotated 180° which also through appropriate connections causes the tube 402 and transfer units 410 and 412 to also rotate 180°. Block 3 and compartment 416 will then be at position (E) and compartment 418 will then be at position (H). Blocks 1 and 2 and 4 and 5 will remain in their positions. Rod 404 is then lowered and the pin 406 pushes downward plate 3 against plate 4 and plate 4 against plate 5 so that plates 3, 4 and 5 shift into positions (F), (G) and (H) respectively. Block 5 can move into position (H) because compartment 418 is in position (H). Thereafter, rod 404 is then rotated 180° causing tube 402 and transfer units 410 and 412 to also rotate 180° so that now block 5 in compartment 418 is in position (A) and empty compartment 416 is in position (D). The pins 406 and 408 will be in the opposite ends of the respective compartments as that shown in FIG. 16. Rod 404 is then moved upward and the pin 408 will push block 5 against block 1 and block 1 against block 2 so that blocks 5, 1 and 2 will shift into positions (B), (C) and (D) respectively. The continual operation of the lift bar mechanism as described will transfer the plates from the coating section conveyors up to the respective dryer in each of the coating sections. One skilled in the art would easily understand how the described mechanism can be adapted to be used to lower plates from the dryers to the conveyors.

While the invention has been particularly shown and described with respect to the illustrative and preferred embodiments thereof, it will be understood by those skilled in the art that the foregoing and other changes in form and details may be made therein without departing from the spirit and scope of the invention which should be limited only by the scope of the appended claims.

What is claimed is:

1. An apparatus for coating a product comprising:

one or more plate means for receiving and retaining a plurality of product;

conveyor means for incrementally advancing said one or more plate means;

a coating tank;

dipping means for lowering and raising at least one of said one or more plate means into said coating tank for forming a coating on at least a portion of the product;

rotating means for rotating at least one of said one or more plate means containing said coated product after said coating is formed on at least a portion of the product;

dryer means for drying said coating and having a first section and a second section;

a plurality of space guide means disposed in each of said first and second sections of said dryer means;

first elevator means for transferring said one or more plate means from said conveyor means to said dryer means;

transporting means for transporting said one or more plate means through said first and second sections of said dryer means, said transporting means comprises means for transporting said one or more plate means in a substantially horizontal first direction along a first of said plurality of spaced guide means, and in a second opposite, substantially horizontal direction along a second of said spaced guide means, and for transferring said one or more plate means between said first and second spaced guide means; and second elevator means for transferring said one or more plate means from said dryer means to said conveyor means.

2. The apparatus of claim 1 wherein said first elevator means comprises:

a plurality of intermediate plate retaining means for holding said one or more plates means at positions intermediate to said conveyor means and said dryer means; and first lift bar means for raising said one or more plate means incrementally from said conveyor means to said one or more intermediate plate retaining means.

3. The apparatus of claim 2 wherein said plate means has at least one side edge and said intermediate plate retaining means comprises a plurality of channel means for engaging at least one side edge of said plate means.

4. The apparatus of claim 3 wherein said first elevator means further comprises means for moving said first lift bar means and said intermediate plate retaining means in a total of four orthogonal directions, the completion of movement in each of the four directions moving each of said one or more plate means from one intermediate retaining means to the next highest intermediate plate retaining means.

5. The apparatus of claim 4 wherein said second elevator means comprises:

a plurality of intermediate plate retaining means for holding said one or more plate means at a position intermediate to said dryer means and said conveyor means; and second lift bar means for lowering said one or more plate means incrementally from said dryer means to said one or more intermediate plate retaining means.

6. The apparatus of claim 5 wherein said intermediate plate retaining means of said second elevator means comprises a plurality of channel means for engaging at least one side edge of said plate means.

7. The apparatus of claim 6 wherein said second elevator means further comprises means for moving said second lift bar means and said intermediate plate retaining means in a total of four orthogonal directions, the completion of movement in each of the four directions moving each of said one or more plate means from one intermediate retaining means to the next highest intermediate plate retaining means.

8. The apparatus of claim 1 wherein said plurality of guide means are vertically spaced and horizontally disposed in each of said first and second sections of said dryer.

9. The apparatus of claim 8 wherein said transporting means comprises at least one pair of pusher bars for moving said one or more plate means horizontally along one or more of said plurality of vertically spaced guide means.

10. The apparatus of claim 9 wherein said transporting means comprises means for vertically transferring said one or more plate means between one or more of said vertically spaced guide means.

11. The apparatus of claim 10 wherein said transferring means includes a plurality of channel means mounted to a lift bar means.

12. The apparatus of claim 11 wherein said transporting means further comprises mid-elevator means interposed between said first and second sections of said drier means for transferring at least one plate means upward between said vertically spaced guide means in said first section and downward between said vertically spaced guide means in said second section.

13. The apparatus of claim 11 wherein said first and second elevator means comprises a continuous chain lifting means having a plurality of channel means for engaging side edges of said plate means.

14. The apparatus of claim 13 wherein said plurality of guide means are vertically spaced and horizontally disposed in each of said first and second sections of said dryer.

15. The apparatus of claim 14 wherein said transporting means includes at least one pair of pusher bars for moving said one or more plate means horizontally along one or more of said plurality of vertically spaced guide means.

16. The apparatus of claim 15 wherein said transporting means includes means for vertically transferring said one or more plate means between one or more of said vertically spaced guide means, 17. The apparatus of claim 16 wherein said transporting means further comprises mid-elevator means interposed between said first and second sections of said dryer means for transferring at least one plate means upward between said vertically spaced guide means in said first section and downward between said vertically spaced guide means in said second section.

18. The apparatus of claim 1 wherein said plate means has at least one side edge and said first and second elevator means comprise lift rod means having a plurality of channel means for engaging said at least one side edge of said plate means.

19. The apparatus of claim 18 wherein said plurality of guide means are vertically spaced and horizontally disposed in each of said first and second sections of said dryer, 20. The apparatus of claim 19 wherein said transporting means comprises at least one pair of pusher bars for moving said one or more plate means horizontally along one or more of said plurality of guide means.

21. The apparatus of claim 20 wherein said transporting means includes means for vertically transferring said one or more plate means between one or more of said vertically spaced guide means.

22. The apparatus of claim 21 wherein said transporting means further comprises mid-elevator means interposed between said first and second sections of said dryer means for transferring at least one plate means upward between said vertically spaced guide means in said first section and downward between said vertically spaced guide means in said second section.

\* \* \* \* \*